United States Patent
Bar-Or et al.

(10) Patent No.: US 8,916,568 B2
(45) Date of Patent: *Dec. 23, 2014

(54) METHOD OF USING DIKETOPIPERAZINES AND COMPOSITION CONTAINING THEM

(71) Applicant: Ampio Pharmaceuticals, Inc., Greenwood Village, CO (US)

(72) Inventors: David Bar-Or, Englewood, CO (US); C. Gerald Curtis, Cardiff (GB); Nagaraja K. R. Rao, Cardiff (GB); Greg Thomas, Highlands Ranch, CO (US)

(73) Assignee: Ampio Pharmaceuticals, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/012,330

(22) Filed: Aug. 28, 2013

(65) Prior Publication Data

US 2013/0345238 A1  Dec. 26, 2013

Related U.S. Application Data

(63) Continuation of application No. 13/252,377, filed on Oct. 4, 2011, which is a continuation of application No. 10/397,964, filed on Mar. 25, 2003, now Pat. No. 8,455,517, which is a continuation of application No. 09/922,234, filed on Aug. 2, 2001, now Pat. No. 6,555,543.

(60) Provisional application No. 60/222,849, filed on Aug. 4, 2000.

(51) Int. Cl.
  *A61K 31/497* (2006.01)
  *A61K 31/495* (2006.01)
  *A61K 31/496* (2006.01)

(52) U.S. Cl.
  CPC ............ *A61K 31/495* (2013.01); *A61K 31/496* (2013.01)
  USPC .................. 514/255.02; 514/252.12; 514/557

(58) Field of Classification Search
  None
  See application file for complete search history.

(56) References Cited

U.S. PATENT DOCUMENTS

| | | | |
|---|---|---|---|
| 3,928,330 A | 12/1975 | Ramey et al. | |
| 3,941,790 A | 3/1976 | Creighton | |
| 3,976,773 A | 8/1976 | Curran | |
| 4,006,261 A | 2/1977 | Pickenhagen et al. | |
| 4,088,649 A | 5/1978 | Smith et al. | |
| 4,205,057 A | 5/1980 | Whitaker | |
| 4,289,759 A | 9/1981 | Heavner et al. | |
| 4,312,987 A | 1/1982 | Beck | |
| 4,331,595 A | 5/1982 | Heavner et al. | |
| 4,661,500 A | 4/1987 | Rozencwaig | |
| 4,694,061 A | 9/1987 | Pfeifer | |
| 4,694,081 A | 9/1987 | Miller et al. | |
| 4,771,056 A | 9/1988 | Rozencwaig | |
| 4,806,538 A | 2/1989 | Shimazaki et al. | |
| 4,886,796 A | 12/1989 | Eichner et al. | |
| 4,940,709 A | 7/1990 | Shimazaki et al. | |
| 4,992,552 A | 2/1991 | Hubbs et al. | |
| 5,047,401 A | 9/1991 | Lipsky et al. | |
| 5,144,073 A | 9/1992 | Hubbs | |
| 5,238,938 A | 8/1993 | Tone et al. | |
| 5,358,938 A | 10/1994 | Cai et al. | |
| 5,418,218 A | 5/1995 | Wilber | |
| 5,434,151 A | 7/1995 | Cai et al. | |
| 5,463,083 A | 10/1995 | Biftu et al. | |
| 5,503,852 A | 4/1996 | Steiner et al. | |
| 5,512,544 A | 4/1996 | Wallach et al. | |
| 5,538,993 A | 7/1996 | Mechoulam et al. | |
| 5,543,402 A | 8/1996 | Bosies et al. | |
| 5,543,503 A | 8/1996 | Chuntharapai et al. | |
| 5,545,404 A | 8/1996 | Page | |
| 5,550,132 A | 8/1996 | Benson et al. | |

(Continued)

FOREIGN PATENT DOCUMENTS

| | | |
|---|---|---|
| CS | 254868 | 6/1987 |
| CZ | 2827.94 | 4/1996 |

(Continued)

OTHER PUBLICATIONS

FR2717484, machine translation accessed from espacenet.com on Oct. 6, 2013.*

(Continued)

*Primary Examiner* — James D Anderson
*Assistant Examiner* — Stephanie Springer
(74) *Attorney, Agent, or Firm* — Sheridan Ross P.C.

(57) ABSTRACT

The invention provides a method of inhibiting the effects of platelet activating factor (PAF). For instance, a disease or condition mediated by PAF (particularly inflammation) can be treated or platelet aggregation can be inhibited. The invention also provides a method of inhibiting the production and/or release of interleukin 8 (IL-8) by cells. The effects of PAF and the production and/or release of IL-8 are inhibited according to the invention by a compound of the formula:

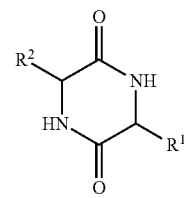

wherein $R^1$ and $R^2$ are defined in the application, or a physiologically-acceptable salt thereof. The invention also provides pharmaceutical compositions comprising these compounds.

5 Claims, No Drawings

(56) References Cited

U.S. PATENT DOCUMENTS

| | | | |
|---|---|---|---|
| 5,578,323 | A | 11/1996 | Milstein et al. |
| 5,589,501 | A | 12/1996 | Carrera et al. |
| 5,648,486 | A | 7/1997 | Cai et al. |
| 5,693,338 | A | 12/1997 | Milstein |
| 5,700,804 | A | 12/1997 | Collins et al. |
| 5,703,093 | A | 12/1997 | Cai et al. |
| 5,741,809 | A | 4/1998 | Biftu et al. |
| 5,750,530 | A | 5/1998 | Bryans et al. |
| 5,750,565 | A | 5/1998 | Cai et al. |
| 5,776,892 | A | 7/1998 | Counts et al. |
| 5,780,503 | A | 7/1998 | Biftu et al. |
| 5,792,776 | A | 8/1998 | Biftu et al. |
| 5,817,751 | A | 10/1998 | Szardenings et al. |
| 5,834,032 | A | 11/1998 | Song |
| 5,843,950 | A | 12/1998 | Tasaka et al. |
| 5,856,323 | A | 1/1999 | Cai et al. |
| 5,877,174 | A | 3/1999 | Ono et al. |
| 5,883,227 | A | 3/1999 | Kline et al. |
| 5,886,152 | A | 3/1999 | Nakatani et al. |
| 5,902,812 | A | 5/1999 | Brocchini et al. |
| 5,919,785 | A | 7/1999 | Dinsmore et al. |
| 5,932,112 | A | 8/1999 | Browning, Jr. |
| 5,932,579 | A | 8/1999 | Campbell et al. |
| 5,976,569 | A | 11/1999 | Milstein |
| 5,985,581 | A | 11/1999 | Nixon et al. |
| 5,990,112 | A | 11/1999 | Campbell et al. |
| 6,034,057 | A | 3/2000 | Dutta |
| 6,034,221 | A | 3/2000 | Berezenko et al. |
| 6,060,452 | A | 5/2000 | Green et al. |
| 6,090,780 | A | 7/2000 | Prasad |
| 6,096,737 | A | 8/2000 | Loder |
| 6,099,856 | A | 8/2000 | Milstein et al. |
| 6,107,050 | A | 8/2000 | Alkon et al. |
| 6,180,616 | B1 | 1/2001 | Fukunaga |
| 6,222,029 | B1 | 4/2001 | Edwards et al. |
| 6,248,363 | B1 | 6/2001 | Patel et al. |
| 6,262,119 | B1 | 7/2001 | Ferrante et al. |
| 6,265,535 | B1 | 7/2001 | Greene et al. |
| 6,331,318 | B1 | 12/2001 | Milstein et al. |
| 6,358,957 | B1 | 3/2002 | Fukumoto et al. |
| 6,395,774 | B1 | 5/2002 | Milstein |
| 6,441,172 | B1 | 8/2002 | Nefzi et al. |
| 6,461,875 | B1 | 10/2002 | Bar-Or et al. |
| 6,475,743 | B1 | 11/2002 | Bar-Or et al. |
| 6,492,179 | B1 | 12/2002 | Bar-Or et al. |
| 6,531,505 | B2 | 3/2003 | Xu et al. |
| 6,541,224 | B2 | 4/2003 | Yu et al. |
| 6,555,543 | B2 | 4/2003 | Bar-Or et al. |
| 6,635,649 | B2 | 10/2003 | Teng et al. |
| 6,677,473 | B1 | 1/2004 | Madison et al. |
| 6,689,765 | B2 | 2/2004 | Baroudy et al. |
| 6,815,214 | B2 | 11/2004 | Boyce et al. |
| 6,930,112 | B2 | 8/2005 | Weaver et al. |
| 6,967,202 | B2 | 11/2005 | Rao et al. |
| 7,026,322 | B2 | 4/2006 | Hayashi et al. |
| 7,175,844 | B2 | 2/2007 | King |
| 7,276,534 | B2 | 10/2007 | Milstein |
| 7,288,545 | B2 | 10/2007 | Teng et al. |
| 7,332,153 | B2 | 2/2008 | Bhatia et al. |
| 7,378,403 | B2 | 5/2008 | Kozikowski et al. |
| 7,575,929 | B2 | 8/2009 | Bar-Or et al. |
| 7,732,403 | B2 | 6/2010 | Bar-Or et al. |
| 7,919,497 | B2 | 4/2011 | Palladino et al. |
| 8,030,488 | B2 | 10/2011 | Sviridov et al. |
| 8,067,425 | B2 | 11/2011 | Brimble et al. |
| 8,183,209 | B2 | 5/2012 | Bar-Or et al. |
| 8,217,047 | B2 | 7/2012 | Bar-Or |
| 8,268,830 | B2 | 9/2012 | Bar-Or et al. |
| 8,324,167 | B2 | 12/2012 | Bar-Or et al. |
| 8,440,696 | B2 | 5/2013 | Bar-Or et al. |
| 8,455,517 | B2 | 6/2013 | Bar-Or et al. |
| 8,507,496 | B2 | 8/2013 | Bar-Or |
| 2003/0119750 | A1 | 6/2003 | Demuth et al. |
| 2003/0153575 | A1 | 8/2003 | Orme et al. |
| 2003/0157030 | A1 | 8/2003 | Davis et al. |
| 2003/0187226 | A1 | 10/2003 | Goddey et al. |
| 2003/0203915 | A1 | 10/2003 | Fang et al. |
| 2004/0024180 | A1 | 2/2004 | Drauz et al. |
| 2004/0038865 | A1 | 2/2004 | Gelber et al. |
| 2004/0063654 | A1 | 4/2004 | Davis et al. |
| 2005/0096323 | A1 | 5/2005 | Cheng et al. |
| 2005/0249681 | A1 | 11/2005 | Heidenfelder et al. |
| 2007/0060508 | A1 | 3/2007 | Haberl et al. |
| 2007/0208087 | A1 | 9/2007 | Sanders et al. |
| 2008/0017576 | A1 | 1/2008 | Belfort et al. |
| 2008/0260838 | A1 | 10/2008 | Hokenson et al. |
| 2010/0120056 | A1 | 5/2010 | Bar-Or et al. |
| 2010/0144611 | A1 | 6/2010 | Bar-Or et al. |
| 2010/0190696 | A1 | 7/2010 | Bar-Or et al. |
| 2012/0022081 | A1 | 1/2012 | Bar-Or et al. |
| 2012/0058934 | A1 | 3/2012 | Bar-Or |
| 2012/0094918 | A1 | 4/2012 | Bar-Or et al. |
| 2012/0157473 | A1 | 6/2012 | Bar-Or |
| 2013/0090292 | A1 | 4/2013 | Bar-Or et al. |

FOREIGN PATENT DOCUMENTS

| | | | |
|---|---|---|---|
| CZ | 280726 | | 4/1996 |
| CZ | 2000-2680 | | 7/2000 |
| CZ | 2000-2681 | | 7/2000 |
| DE | 19937721 | | 2/2001 |
| EP | 0043219 | | 1/1982 |
| EP | 0181152 | | 5/1986 |
| EP | 0214557 | | 3/1987 |
| EP | 0216746 | | 4/1987 |
| EP | 0220958 | | 5/1987 |
| EP | 0493812 | | 7/1992 |
| EP | 0557388 | | 9/1993 |
| EP | 0610943 | | 8/1994 |
| EP | 0655060 | | 5/1995 |
| EP | 0835660 | | 4/1998 |
| EP | 0939124 | | 9/1999 |
| EP | 1445323 | | 8/2004 |
| FR | 2717484 | | 9/1995 |
| FR | 2717484 | A1 * | 9/1995 |
| GB | 2263109 | | 7/1993 |
| GB | 2372740 | | 9/2002 |
| JP | 59-73574 | | 4/1984 |
| JP | 61-112060 | | 5/1986 |
| JP | 62-036331 | | 2/1987 |
| JP | 63-290868 | | 11/1988 |
| JP | 01-013075 | | 1/1989 |
| JP | 3176478 | | 7/1991 |
| JP | 05-163148 | | 6/1993 |
| JP | 07-247474 | | 9/1995 |
| JP | 08-277203 | | 10/1996 |
| JP | 10-226615 | | 8/1998 |
| JP | 10-245315 | | 9/1998 |
| JP | 11-504509 | | 4/1999 |
| JP | 2000-327575 | | 11/2000 |
| NZ | 218088 | | 1/1989 |
| NZ | 335544 | | 8/2001 |
| RU | 2112242 | | 5/1998 |
| RU | 2125728 | | 1/1999 |
| RU | 2128840 | | 4/1999 |
| WO | WO 91/14378 | | 10/1991 |
| WO | WO 93/08815 | | 5/1993 |
| WO | WO 94/04512 | | 3/1994 |
| WO | WO 94/04513 | | 3/1994 |
| WO | WO 94/04537 | | 3/1994 |
| WO | WO 94/20063 | | 9/1994 |
| WO | WO 95/03054 | | 2/1995 |
| WO | WO 95/18610 | | 7/1995 |
| WO | WO 96/00212 | | 1/1996 |
| WO | WO 96/00391 | | 1/1996 |
| WO | WO 96/10396 | | 4/1996 |
| WO | WO 96/32478 | | 10/1996 |
| WO | WO 97/12625 | | 4/1997 |
| WO | WO 97/36888 | | 10/1997 |
| WO | WO 97/38011 | | 10/1997 |
| WO | WO 97/48685 | | 12/1997 |
| WO | WO 98/09968 | | 3/1998 |
| WO | WO 98/40748 | | 9/1998 |
| WO | WO 99/40931 | | 8/1999 |

(56) References Cited

FOREIGN PATENT DOCUMENTS

| | | |
|---|---|---|
| WO | WO 99/49865 | 10/1999 |
| WO | WO 99/51256 | 10/1999 |
| WO | WO 99/51720 | 10/1999 |
| WO | WO 00/20454 | 4/2000 |
| WO | WO 00/20840 | 4/2000 |
| WO | WO 00/22439 | 4/2000 |
| WO | WO 00/43000 | 7/2000 |
| WO | WO 00/57187 | 9/2000 |
| WO | WO 01/34586 | 5/2001 |
| WO | WO 01/91713 | 12/2001 |
| WO | WO 02/11676 | 2/2002 |
| WO | WO 02/12201 | 2/2002 |
| WO | WO 02/059604 | 8/2002 |
| WO | WO 02/062797 | 8/2002 |
| WO | WO 02/083667 | 10/2002 |
| WO | WO 02/089738 | 11/2002 |
| WO | WO 03/032809 | 4/2003 |
| WO | WO 03/045395 | 6/2003 |
| WO | WO 2004/034060 | 4/2004 |
| WO | WO 2004/048345 | 6/2004 |
| WO | WO 2004/054498 | 7/2004 |
| WO | WO 2005/011699 | 2/2005 |
| WO | WO 2008/008357 | 1/2008 |
| WO | WO 2009/042193 | 4/2009 |
| WO | WO 2012/033789 | 3/2012 |

OTHER PUBLICATIONS

"CENTRICON Centrifugal Filter Devices User Guide," Millipore Corp., Mar. 2005, 23 pages.
Cytokines and Autoimmune Diseases, edited by Kuchroo, et al., 2002, Humana Press Inc., Totowa, NJ, pp. 3-23, 389-406.
Cytokines and Autoimmune Diseases, edited by Kuchroo, et al., 2002, Humana Press Inc., Totowa, NJ, pp. 5, 11, and 391.
Database WPI Section Ch, Week 199844 Derwent Publications Ltd., London, GB; AN 1998-515050 XP002369751 & JP 10 226615 A (Pola Chem Ind Inc) Aug. 25, 1998.
"Diabetic Retinopathy—What you should know," National Institutes of Health, 2003, NIH Publication No. 06-2171, 24 pages.
"Disposable PD-10 Desalting Columns," GE Healthcare Life Sciences, downloaded Nov. 1, 2011, 2 pages.
"Desalting and buffer exchange with Sephadex® G-25," Amersham Biosciences, downloaded from www.gelifesciences.com on Jan. 8, 2013, 8 pages.
"Freeze-Drying (Lyophilization)," Remington: The Science and Practice of Pharmacy—21st Edition, Lippencott Williams and Wilkins, 2005, p. 828.
"Human Albumin," Sigma downloaded from www.sigmaaldrich.com on Jan. 8, 2013, 1 page.
Online Medical Dictionary definition of albumin, medical-dictionary.thefreedictionary.com/albumin, downloaded Nov. 1, 2011, 4 pages.
The Cytokine Handbook, edited by Thomson and Lotze, 4th edition, 2003 Academic Press, vol. I, London, UK, pp. 169, 186, 187, 467, 570, 571, 838, 839, 1189-1193, 1197-1200.
The Cytokine Handbook, edited by Thomson and Lotze, 4th edition, 2003 Academic Press, vol. II, London, UK, pp. 838-860 and 1189-1211.
The Cytokine Handbook, edited by Thomson and Lotze, 4th edition, 2003 Academic Press, vol. I, London, UK, pp. 167-199, 456-474, 567-601.
The Dictionary of Immunology, Fourth Edition, Edited by Herbert et al., 1995, pp. 51-52 and 69.
"Tryprostatin A, Aspergillus fumigates," available at www.emdbiosciences.com/Products/ProductDisplay.asp?catno=649305&, printed on Jun. 21, 2006, 1 page.
Abraha et al., "C-terminal inhibition of tau assembly in vitro and in Alzheimer's disease," Journal of Cell Science, 2000, vol. 113, pp. 3737-3745.
Acharya et al., "Solid-phase synthesis of substituted imidazoline-tethered 2,3-diketopiperazines, cyclic ureas, and cyclic thioureas," J Comb Chem, Nov.-Dec. 2001, vol. 3(6), pp. 612-623.
Adorini, L., "Selective immunointervention in autoimmune diseases: lessons from multiple sclerosis," J Chemother, Jun. 2001, vol. 13(3), pp. 219-234 (Abstract Only Provided).
Akiyama et al., "Inflammation and Alzheimer's disease," Neurobiol Aging, 2000, vol. 21, pp. 383-421.
Albert et al., "ABT-491, a highly potent and selective PAF antagonist, inhibits nasal vascular permeability associated with experimental allergic rhinitis in Brown Norway rats," Inflamm. Res., 1997, Supplement 2, pp. S133-S134.
Alvarez et al., "Isolation and Structure Elucidation of Two New Calpain Inhibitors from Streptomyces griseus," J. Antibiotics, Nov. 1994, vol. 47(11), pp. 1195-1201.
Andreasen et al., "Cerebrospinal fluid beta-amyloid (1-42) in Alzheimer disease: differences between early- and late-onset Alzheimer disease and stability during the course of disease," Arch. Neurol., Jun. 1999, vol. 56(6), pp. 673-680.
Arbabi et al., "Priming Interleukin 8 Production: Role of Platelet-Activating Factor and p38," Arch Surg., Dec. 1999, vol. 134(12), pp. 1348-1353.
Ashwood et al. "Is autism an autoimmune disease?" Autoimmunity Reviews, Nov. 2004, vol. 3, No. 7-8, pp. 557-562.
Au et al., "Effect of PDE4 Inhibitors on Zymosan-Induced IL-8 Release From Human Neutrophils: Synergism with Prostanoids and Salbutamol," Br. J. Pharmacol, 1998, vol. 123, pp. 1260-1266.
Bagaria et al., "Cyclo(L-leucyl-alpha,beta-dehydrophenylalanine): the first diketopiperazine containing an alpha,beta-dehydrophenylalanine residue," Acta Crystallogr C., Mar. 2005, vol. 61(Pt 3), pp. 174-176, Epub Feb. 28, 2005.
Baig et al., "High Performance Liquid Chromatography as a Tool in the Definition of Abnormalities in Monamine and Tryptophan Metabolites in Cerebrospinal Fluid from Patients with Neurological Disorders," Biomed Chromatogr 1991, 5(3):108-112 (Abstract Only Provided).
Balk, "Lesson 24, vol. 12—ARDS: Pathophysiology of SIRS and MODS" www.chestnet.org/education/pccu/vol12/ lesson24.html, pp. 1-19, printed Jul. 20, 2000.
Banks et al., "Radioactively Iodinated Cyclo(His-Pro) Crosses the Blood-Brain Barrier and Reverses Ethanol-Induced Narcosis," Am J Physiol, May 1993, vol. 264(5 Pt. 1), pp. E723-E729 (Abstract Only Provided).
Bar-Or et al., "An Analog of the Human Albumin N-Terminus (Asp-Ala-His-Lys) Prevents Formation of Copper-Induced Reactive Oxygen Species," Biochemical and Biophysical Research Communications, 2001, vol. 284(3), pp. 856-862.
Bar-Or et al. "Commercial human albumin preparations for clinical use are immunosuppressive in vitro," Critical Care Medicine, Jun. 2006, vol. 34, No. 6, pp. 1707-1712.
Bar-Or et al., "Potential Plasma Surrogate Biomakers for CNS Demyelinating Processes," 19th Congress of the European Committee for Treatment and Research in Multiple Sclerosis Meeting; Sep. 17-20, 2003; 2 pp. (Abstract first distributed at the meeting; attached is poster presented at meeting).
Barrow et al., WIN 64821, a New Competitive Antagonist to Substance P, Isolated from an Aspergillus Species: Structure Determination and Solution Conformation, J. Org. Chem., 1993, vol. 58, pp. 6016-6021.
Battersby et al., "Diketopiperazine Formation and N-Terminal Degradation in Recombinant Human Growth Hormone," Int. J. Pept. Protein Res, Sep. 1994, vol. 44(3), pp. 215-222 (Abstract Only Provided).
Berman et al., "Psoriasis," PubMed Health, reviewed Nov. 22, 2011, available at www.ncbi.nlm.nih.gov/pubmedhealth/PMH0001470/?report=printable.
Berry et al., "Inhibition of Tau Polymerization by its Carboxy-Terminal Caspase Cleavage Fragment," Biochemistry, 2003, vol. 42, pp. 8325-8331.
Bhargava, "Antagonism of ketamine-induced anesthesia and hypothermia by thyrotropin releasing hormone and cyclo (His-Pro)," Neuropharmacology, 1981, vol. 20(7), pp. 699-702.
Bhargava, "Inhibition of abstinence syndrome in opiate dependent mice by cyclo (His-Pro)," Life Sci, 1981, vol. 28(11), pp. 1261-1267.

(56) References Cited

OTHER PUBLICATIONS

Bhargava et al., "Inhibition of Neuroleptic-Induced Dopamine Receptor Supersensitivity by Cyclo (Leu-Gly)," Pharmacol Biochem Behav, Nov. 1980, vol. 13(5), pp. 633-636 (Abstract Only Provided).

Bhargava, "The effect of melanotrophin release inhibiting factor (MIF) and cyclo (Leu-Gly) on the tolerance to morphine-induced antinociception in the rat: a dose-response study," Br J Pharmacol, Apr. 1981, vol. 72(4) (Abstract Only Provided).

Bhargava, "The effects of thyrotropin releasing hormone and histidyl-proline diketopiperazine on delta-9-tetrahydrocannabinol-induced hypothermia," Life Sci, 1980, vol. 26(11), pp. 845-850.

Bielekova et al., "Development of biomarkers in multiple sclerosis," Brain, Jul. 2004, vol. 127(Pt 7), pp. 1463-1478, Epub Jun. 4, 2004.

Binisti et al., "Structure-Activity Relationships in Platelet Activating Factor," J. Lipid Mediat. Cell Signal, Jan. 1997, vol. 15(2), pp. 125-144 (Abstract Only Provided).

Blazickova et al., "Immunomodulatory Characteristics of Synthetic Cyclic Dipeptides," Int. J. Immunotherapy, 1994, vol. 10(3), pp. 89-93.

Borthwick, "2,5-Diketopiperazines: Synthesis, Reactions, Medicinal Chemistry, and Bioactive Natural Products," Chemical Reviews, 2012, vol. 112, Iss. 7, pp. 3641-3716.

Bowden et al., "Re-evaluation of histidyl-proline diketopiperazine [cyclo (His-Pro)] effects on food intake in the rate," Pharmacol. Biochem. Behav., Feb. 1988, vol. 29(2), pp. 357-363 (Abstract Only Provided).

Brauns et al., "Selected cyclic dipeptides inhibit cancer cell growth and induce apoptosis in HT-29 colon cancer cells," Anticancer Research, 2004, vol. 24, pp. 1713-1720.

Bressan et al., "Coordination chemistry of peptides. Part II. Crystal structure of cyclo-L-methionylglycine and studies of metal complexation," Int J Pept Protein Res, Apr. 1982, vol. 19(4) (Abstract Only Provided).

Bresser et al., "T-Cell Activation in the Lungs of Patients With Systemic Sclerosis and Its Relation With Pulmonary Fibrosis," Chest, Jul. 2001, 6 pages.

Bunn, "Early detection of lung cancer using serum RNA or DNA markers: ready for "prime time" or for validation?," J Clin Oncol., Nov. 1, 2003, vol. 21(21), pp. 3891-3893.

Caballero et al., "Brief synthesis of the cell cycle inhibitor tryprostatin B and its alanine analogue," Fourth International Electronic conference of Synthetic Organic Chemistry (ECXOC-4), Sep. 1-13, 2000, 4 pages, available at pages.unibas.ch/mdpi/eecxoc-4/c0023/c0023.htm.

Caballero et al., "Brief total synthesis of the cell cycle inhibitor tryprostatin B and related preparation of its alanine analogue," J Org Chem, Sep. 5, 2003, vol. 68(18) (Abstract Only Provided).

Carlton et al., "Attenuation of alcohol-induced hypothermia by cycle (His-Pro) and its analogs," Neuropeptides, Jun. 1995, vol. 28(6), pp. 351-355 (Abstract Only Provided).

Chan et al., "Site-Specific N-Terminal Auto-Degradation of Human Serum Albumin," Eur. J. Biochem., 1995, vol. 227, pp. 524-528.

Chen et al., "Up-regulation of Platelet-activating Factor Receptors in Lung and Alveolar Macrophages in the Bleomycin-Hamster Model of Pulmonary Fibrosis," J. Pharmacol. Exp. Ther., 1997, vol. 280(3), pp. 1219-1227.

Ciarkowski et al., "Conformation of cyclo-(D-phenylalanyl-trans-4-fluoro-D-prolyl)," Int. J. Pept. Protein Res., vol. 36, Sep. 1990, pp. 285-291.

Clark et al., "Roquefortine E, a Diketopiperazine from an Australian Isolate of *Gymnoascus reessii*," J. Nat. Prod., 2005, vol. 68(11), p. 1661-1664 (Abstract Only Provided).

Cody et al., "The design of potent and selective inhibitors of thrombin utilizing a piperazinedione template: part 2," Bioorg Med Chem Lett, Sep. 6, 1999, vol. 9(17), pp. 2503-2508.

Coggins et al., "High Affinity Specific Binding of the Thyrotrophin Releasing Hormone Metabolite Histidylproline to Rat Brain Membranes," Neuropeptides, Jan. 1987, vol. 9(1), pp. 83-91 (Abstract Only Provided).

Costa et al., "Aggregation of features of the metabolic syndrome is associated with increased prevalence of chronic complications in Type 2 diabetes," Diabetic Medicine, 2004, vol. 21, Iss. 3, 252-255.

Couladouros et al., "Solid-phase total synthesis of (−)-Phenylhistine and (−)-Aurantiamine. Synthesis of a diverse dehydro-2,5-diketopiperazine library. Part II," Mol Divers., 2005, vol. 9(13), pp. 111-121.

Crowe et al., "The N Terminal Region of Human Tau is Present in Alzheimer's Disease Protein A68 and is Incorporated into Paired Helical Filaments," American Journal of Pathology, 1991, vol. 139(6), pp. 1463-1470.

Cruse et al., "Illustrated Dictionary of Immunology" Second Edition, 2003, pp. 192, 260, 530-531.

Cui et al., "Novel Mammalian Cell Cycle Inhibitors, Tryprostatins A, B and Other Diketopiperazines Produced by *Aspergillus fumigatus* II. Physico-chemical properties and Structures," The Journal of Antibiotics, Jun. 1996, pp. 534-540.

D'Alagni et al. "Effect of Urea on the Optical Rotatory Dispersion of Diketopiperazines of I-Serine, I-Alanine, I-Lysine, I-Valine, and I-Valylglycine." The Journal of Biological Chemistry, Nov. 10, 1969, vol. 244, No. 21, pp. 5843-5848.

Davidson et al., "Autoimmune Diseases," N. Engl. J. Med, 2001, vol. 345(5), pp. 340-350.

Degrassi et al., "Plant Growth-Promoting *Pseudomonas putida* WCS358 Produces and Secretes Four Cyclic Dipeptides: Cross-Talk with Quorum Sensing Bacterial Sensors," Current Microbiology, 2002, vol. 45, pp. 250-254.

De La Cruz et al, "Effect of WEB 2086-BS, an antagonist of platelet-activating factor receptors, on retinal vascularity in diabetic rats," European Journal of Pharmacology, 1998, vol. 360, Iss. 1, pp. 37-42.

Denault et al., "Transcriptional activation of the interleukin-8 gene by platelet-activating factor in human peripheral blood monocytes," Immunology, 1997, vol. 91, pp. 297-302.

Diamanti et al., "Distribution and Characterization of Cyclo (His-Pro)-like Immunoreactivity in the Human Gastrointestinal Tract," Neuropeptides, Mar. 1985, vol. 6(1):21-5 (Abstract Only Provided).

Dirr, K. et al., "The transformation of arginine into citrulline," Z. Physiol. Chem., 1935, vol. 237, pp. 121-130.

Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," Neuropeptides, 1993, vol. 25(6), pp. 357-361 (Abstract Only Provided).

Esposito et al., "The Solution Structure of the C-Terminal Segment of Tau Protein," Journal of Peptide Science, 2000, vol. 6, pp. 550-559.

Evans et al. "Metabolic effects of platelet-activating factor in rats in vivo: Stimulation of hepatic glycogenolysis and lipogenesis." Biochemical Journal, Jul. 1990, vol. 269, No. 1, pp. 269-272.

Faden et al., "Neuroprotective and nootropic actions of a novel cyclized dipeptide after controlled cortical impact injury in mice." J. Cerebral Blood Flow & Metabolism, 2003, vol. 23, pp. 355-363.

Faden et al., "Novel diketopiperazine enhances motor and cognitive recovery after traumatic brain injury in rats and shows neuroprotection in vitro and in vivo," J. Cerebral Blood Flow & Metabolism, 2003, vol. 23, pp. 342-354.

Faden et al., "Novel neuroprotective Tripeptides and Dipeptides," Ann. N.Y. Acad. Sci, 2005, vol. 1053, pp. 472-481.

Faden et al., "Novel small peptides with neuroprotective and nootropic properties," J. Alzheimer's Dis, 2004, vol. 6, pp. S93-S97.

Faden et al., "Novel TRH analog improves motor and cognitive recovery after traumatic brain injury in rodents," Am J Physiol, Oct. 1999, vol. 277(4 Pt 2), pp. R1196-R1204.

Fdhila et al., "dd-diketopiperazines: antibiotics active against *Vibrio anguillarum* isolated form marine bacteria associted with cultures of *Pecten maximus*" J Nat Prod, Oct. 2003, vol. 66(10) (Abstract Only Provided).

Fischer, "Diketopiperazines in Peptide and Combinatorial Chemistry," Journal of Peptide Science, 2003, vol. 9, pp. 9-35.

Folkes et al., "Synthesis and in vitro evaluation of a series of diketopiperazine inhibitors of plasminogen activator inhibitor-1," Bioorg Med Chem Lett, Oct. 2001, vol. 11(19), pp. 2589-2592 (Abstract Only Provided).

(56) References Cited

OTHER PUBLICATIONS

Fragner et al., "A New Biological Contribution of Cyclo(His-Pro) to the Peripheral Inhibition of Pancreatic Secretion," Am J Physiol, Dec. 1997, vol. 273(6 Pt. 1), pp. E1127-E1132 (Abstract Only Provided).
Gamblin et al., "Tau Polymerization: Role of the Amino Terminus," Biochemistry, 2003, vol. 42(7), pp. 2252-2257.
Garcia-Sierra et al., "Conformational Changes and Truncation of Tau Protein during Tangle Evolution in Alzheimer's Disease," Journal of Alzheimer's Disease, 2003, vol. 5, pp. 65-77.
Gomez et al., "Low-Dose Dopamine Agonist Administration Blocks Vascular Endothelial Growth Factor (VEGF)-Mediated Vascular Hyperpermeability without Altering VEGF Receptor 2-Dependent Luteal Angiogenesis in a Rat Ovarian Hyperstimulation Model," Endocrinology, 2006, vol. 147, No. 11, pp. 5400-5411.
Goolcharran et al., "Comparison of the Rates of Deamidation, Diketopiperazine Formation and Oxidation in Recombinant Human Vascular Endothelial Growth Factor and Model Peptides," AAPS PharmSci, 2000 vol. 2(1), p. E5 (Abstract Only Provided).
Gorbitz "Crystal and Molecular Structure of cyclo-L-Aspartyl-L-alanyl (3,6-Dioxo-5-methyl-2- piperazineacetic acid)" Acta Chemica Scandinavica B, 1987, vol. 41, pp. 83-86.
Gorbitz, "Crystal and molecular structures of the isomeric dipeptides alpha-L-aspartyl-L-alanine and beta-L-aspartyl-L-alanine," Acta Chem Scand B., vol. 41(9), Oct. 1987, pp. 679-685.
Gordon et al, "Reductive Alkylation on a Solid Phase: Synthesis of a Piperazinedione Combinatorial Library," Bioorganic & Medicinal Chemistry Letters, 1995, vol. 5, No. 1, p. 47-50.
Gountopoulou et al. "TNFα is a potent inducer of platelet-activating factor synthesis in adipocytes but not in preadipocytes. Differential regulation by PI3K." Cytokine, Jan. 2008, vol. 41, No. 2 p. 174-181, (Abstract Only).
Graz et al "Cyclic Dipeptides in the Induction of Maturation for Cancer Therapy," J. Pharm. Pharmacol., 2000, vol. 52, pp. 75-82.
Graz et al., "Mechanism of a anti-fungal action of selected cyclic dipeptides," Pharmazie, Nov. 2001, vol. 56(11), pp. 900-901.
Gross et al., "Regulation of Interleukin-8 Production in a Human Colon Epithelial Cell Line (HT-29)," Gastroenterology, 1995, vol. 108, pp. 653-661.
Grubek-Jaworska et al., "CD4/CD8 lymphocytes in BALF during the efferent phase of lung delayed-type hypersensitivity reaction induced by single antigen inhalation," Med Sci Monit, Sep.-Oct. 2001, vol. 7(5), pp. 878-883 (Abstract Only Provided).
Gu et al., "Diketopiperazine Formation, Hydrolysis, and Epimerization of the New Dipeptide Angiotensin-Converting Enzyme Inhibitor RS-10085," Pharm Res, 1987, vol. 4(5), pp. 392-397 (Abstract Only Provided).
Gudasheva et al., "Anxiolytic activity of endogenous nootropic dipeptide cycloprolylglycine in elevated plus-maze test," Bull Exp Biot Med, May 2001, vol. 131(5) (Abstract Only Provided).
Gudasheva et al., "Identification of a novel endogenous memory facilitating cyclic dipeptide cyclo-prolylglycine in rat brain," FEBS Lett, Aug. 5, 1996, vol. 391(1-2) (Abstract Only Provided).
Guerra et al., "PEGylation Prevents the N-Terminal Degradation of Megakaryocyte Growth and Development Factor," Pharm Res, 1998, vol. 15(12), pp. 1822-1827 (Abstract Only Provided).
Gustafson, "Adipose Tissue, Inflammation and Atherosclerosis," J. Atheroscler. Thromb., Apr. 30, 2010, vol. 17(4), pp. 332-341.
Hansel et al. "Metabolic Syndrome Is Associated with Elevated Oxidative Stress and Dysfunctional Dense High-Density Lipoprotein Particles Displaying Impaired Antioxidative Activity." The Journal of Clinical Endocrinology & Metabolism, Oct. 2004, vol. 89, No. 10, pp. 4963-4971.
Hasegawa et al., "Protein Sequence and Mass Spectrometric Analysis of Tau in the Alzheimer's Disease Brain," Journal of Biological Chemistry, 1992, vol. 267(24), pp. 17047-17054.
Hayashi et al., "Synthetic Hexa- and Heptapeptides That Inhibit IL-8 from Binding to and Activating Human Blood Neutrophils1," J. Immunol., 1995, vol. 154, pp. 814-824.

Hilton et al., "Food Contains the Bioactive Peptide, Cyclo(His-Pro)," J. Clin Endocrinol Metab, Aug. 1992, vol. 75(2), pp. 375-378 (Abstract Only Provided).
Hilton et al., "Identification and Characterization of Cyclo (His-Pro)-Like Immunoreactivity in Amniotic Fluid," Peptides, Mar.-Apr. 1989, vol. 10(2), pp. 299-301 (Abstract Only Provided).
Hilton et al., "Radioimmunoassay of Cyclo(His-Pro) in Unextracted Human Plasma: Report of a Normal Range and Definition of Factors Critical for Successful Assay," Neuropeptides, 1989, vol. 13(1), pp. 65-70 (Abstract Only Provided).
Hilton et al., "Relationship between Plasma Cyclo (His-Pro), a Neuropeptide Common to Processed Protein-Rich Food, C-Peptide/Insulin Molar Ratio in Obese Women," Nutr Neurosci, 2001, vol. 4(6), pp. 469-474 (Abstract Only Provided).
Hlinak et al., "Effect of alaptide, its analogues and oxiracetam on memory for an elevated plus-maze in mice," European Journal of Pharmacology, 1996, vol. 314, pp. 1-7.
Hoffman et al., "An Enzymatically Stable Peptide with activity in the Central Nervous System: Its Penetration through the Blood-CSF Barrier," Brain Res, Feb. 11, 1977, vol. 122(1), pp. 87-94 (Abstract Only Provided).
Holden et al., "Quorum-sensing cross talk: isolation and chemical characterization of cyclic dipeptides from *Pseudomonas aeruginosa* and other Gram-negative bacteria," Moleclur Microbiology, 1999, vol. 33(6), pp. 1254-1266.
Houston et al., "The cyclic dipeptide CI-4 [cyclo-(I-Arg-d-Pro)] inhibits family 18 chitinases by structural mimicry of a reaction intermediate," Biochem J., Nov. 15, 2002, vol. 368(Pt 1) (Abstract Only Provided).
Hwang et al., "Effects of cyclo (his-pro) plus zinc on glucose metabolism in genetically diabetic obse mice," Diabetes Obes. Metab., Sep. 2003, vol. 5(5), pp. 317-324 (Abstract Only Provided).
Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," Life Sci. 1987, 41(22):2419-2428, Abstract only, from PubMed—PMID:2891013.
Ishibashi et al., "A Mechanism for Bitter Taste Sensibility in Peptides," Agric. Biol. Chem., 1988, vol. 52(3), pp. 819-827.
Ishibashi et al., "Bitterness of Leucine-Containing Peptides," Agric. Biol. Chem., 1987, vol. 51 (9), pp. 2389-2394.
Ishii, et al. "Incidence of brain tumors in rats fed aspartame," Toxicology Letters, 1981, vol. 7, pp. 433-437.
Jackson et al., "Amyotrophic Lateral Sclerosis: Thryrotropin-releasing hormone and histidyl proline diketopiperazine in the spinal cord and cerebrospinal fluid," Neurology, 1986, vol. 36(9), pp. 1218-1223.
Jamie et al., "The effect of the isomers of cyclo(Trp-Pro) on heart and ion-channel activity," J Pharm Pharmacol, Dec. 2002, vol. 54(12) (Abstract Only Provided).
Jara et al., "Elevated serum levels of cyclo (His-Pro), and endogenous inhibitor ofpituitary prolactin secretion, in systemic lupus erythematosus patients," Lupus, 1997, vol. 6(3) (Abstract Only Provided).
Jaspan et al., "Study of Passage of Peptides Across the Blood-Brain Barrier: Biological Effects of Cyclo(His-Pro) After Intravenous and Oral Administration," Annals of the New York Academy of Science, 1994, vol. 739, pp. 101-107 (Abstract Only Provided).
Jiang et al. "Asymmetric Reformastky reaction catalyzed by amino acid derivatives," Huaxue Tongbao CKNI, 2001, vol. 10, pp. 637-640 (English Abstract).
Jicha et al., "Sequence Requirements for Formation of Conformational Variants of Tau Similar to Those Found in Alzheimer's Disease," Journal of Neuroscience Research, 1999, vol. 55, pp. 713-723.
Kaakkola et al., "Effects of two diketopiperazines, cyclo (His-Pro) and cyclo (Asp-Phe), on striatal dopamine: A microdialysis study," Brain Research Bulletin, 1993, vol. 32(6), pp. 667-672.
Kanzaki et al., "Enzymatic synthesis of dehydro cyclo(His-Phe)s, analogs of the potent cell cycle inhibitor, dehydrophenylahistin, and their inhibitory activities toward cell division," Biosci. Biotechnol Biochem, Nov. 2004, vol. 68(11), pp. 2341-2345 (Abstract Only Provided).

(56) References Cited

OTHER PUBLICATIONS

Kasperska-Zajac et al. "Platelet Activating Factor as a Mediator and Therapeutic Approach in Bronchial Asthma." Inflammation, Apr. 2008, vol. 31, No. 2, pp. 112-120.

Kikwai et al, "Stability and degradation profiles of Spantide II in aqueous solutions," Eur J Pharm Sci, Feb. 2006, vol. 27(2-3), pp. 158-166, Epub Nov. 2, 2005. (Abstract Only Provided).

Kilian et al., "Biological activity of selected tyrosine-containing 2,5-diketopiperazines," Pharmazie, Apr. 2005, vol. 60(4), pp. 305-309 (Abstract Only Provided).

Kilian et al., "The effect of the isomer of cyclo(Trp-Pro) on heart and ion-channel activity," J. Pharm. Pharmacol., Dec. 2002, vol. 54(12), pp. 1659-1665 (Abstract Only Provided).

Kobayashi et al., "Neuropeptide Y and histidyl-proline diketopiperazine," Rinsho-Kensa, Japan, Sep. 1987, vol. 21, No. 9, pp. 984-991.

Kopple et al. "Conformation of Cyclo-(1-Threonine)2 and Cyclo-(I-Allo Threonine)2 : A Proton and Carbon N.m.r. Study." International Journal of Peptide Protein Research, Jul. 1981, vol. 18, No. 1, pp. 33-40.

Koskinen, "Effect of Low Intravenous Doses of TRH, Acid-TRH and Cyclo (His-Pro) on Cerebral and Peripheral Blood Flows," British Journal of Pharmacology, 1986, vol. 87(3), pp. 509-519 (Abstract Only Provided).

Kow et al., "The Effects of the TRH Metabolite Cyclo(His-Pro) and Its Analogs on Feeding," Pharmacology, Biochemistry & Behavior, 1991, vol. 38, pp. 359-364.

Kuenz et al., "Plasma levels of soluble adhesion molecules sPECAM-1, sP-selectin and sE-selectin are associated with relapsing-remitting disease course of multiple sclerosis," J. Neuroimmunol, Oct. 2005, vol. 167(1-2), pp. 143-149.

Kulikov et al., "Review: The Bioregulatory Role of Platelet-Activating Factor in Intracellular Processes and Cell-Cell Interactions," 1997, www.protein.bio.msu.su/biokhimiya/contents/v63/full/63010057.html, pp. 1-13.

Kurahashi et al., "Histydyl-Proline Diketopiperazine (HPD), A Metabolite of Thyrotropin-Releasing Hormone (TRH), Improves the Ataxic Gait in 3-Acetylpyridine (3-AP) Treated Rats," No To Shinkei, Sep. 1986, vol. 38(9), pp. 893-898 (Abstract Only Provided).

Larsen et al. "Kinetics of degradation and oil solubility of ester prodrugs of a model dipeptide (Gly-Phe)," Eur J Pharm Sci, Aug. 2004, vol. 22(5), pp. 399-408 (Abstract Only Provided).

Lechan et al., "Thyrotropin Releasing Hormone but not Histidyl-Proline Diketopiperazine is Depleted from Rat Spinal Cord Following 5,7-Dihydroxytryptamine Treatment," Brain Research, 1985, vol. 326(1), pp. 152-155 (Abstract Only Provided).

Lechin et al., "Plasma Neurotransmitters and Cortisol in Chronic Illness: Role of Stress," J Medicine, 1994, vol. 25(3-4), pp. 181-192 (Abstract Only Provided).

Leduque et al., "Histidyl-Proline Diketopiperazine (His-Pro DKP) Immunoreactivity is Present in the Glucagon-Containing Cells of the Human Fetal Pancreas," J Clin Invest, 1987, 79(3):875-880 (Abstract Only Provided).

Lee et al., "Characterization of an Elastase Inhibitor Produced by *Streptomyces lavendulae* SMF11," Journal of Microbiology and Biotechnology, 2000, vol. 10, No. 1, pp. 81-85.

Lee et al., "Cyclo (Leu-Gly attenuates the striatal dopaminergic supersensitivity induced by chronic morphine," Alcohol Drugs Res, 1987, vol. 7(1) (Abstract Only Provided).

Lehninger et al., "Amino Acids and Peptides," Chapter 5 of Principles of Biochemistry, 1993, 2nd edition, pp. 111-133.

Lindner et al., "[Effects of cyclic adenosine-3',5'-monophosphate and cyclo{Lys-Pro}.HCl neuronotrophic factors in tissue culture]," J Hirnforsch, 1987, vol. 28(3) (Abstract Only Provided).

Liu et al., "Hydroxyprolylserine derivatives JBP923 and JBP485 exhibit the antihepatitis activities after gastrointestinal absorption in rats," J Pharmacol Exp Ther, Aug. 2000, vol. 294(2) (Abstract Only Provided).

Luca et al., "Determination of serotonin content and ceruloplasmin activity, of blood and CSF amino acid level in multiple sclerosis," Neurol Psychiatr (Bucur), 1986, vol. 24(3), pp. 153-159.

Lucietto et al., "The biological activity of the histidine-containing diketopiperazines cyclo (His-Ala) and cyclo (His-Gly)," Peptides, Nov. 2006, vol. 27(11), pp. 2706-2714, Epub Jun. 21, 2006 (Abstract Only Provided).

Mayer, "Immunology—Chapter Four," Immunoglobulins—Structure and Function, online at pathmicro.med.sc.edu/mayer/IgStruct2000.htm, University of South Carolina School of Medicine, Nov. 6, 2009, 8 pages.

Mazza et al., "Potential energy calculations on phenylalanine rotamers in different boat forms of proline-containing cyclic dipeptides," Int. J. Pept. Protein Res., vol. 31, Feb. 1988, pp. 157-163.

McCain et al., "Endorphinergic modulation of immune function: potent action of the dipeptide glycyl-L-glutamine," Life Science, 1987, vol. 41, pp. 169-176.

McCain et al., "Modulation of Human T-Cell Suppressor Activity by Beta Endorphin and Glycyl-L-Glutamine," Int. J. Immunopharmoc, 1986, vol. 8(4), pp. 443-446.

McCleland et al., "An investigation into the biological activity of the selected histidine-containing diketopieperazines cyclo(His-Phe) and cyclo(His-Tyr)," Journal of Pharmacy and Pharmacology, Sep. 2004, vol. 56(9), pp. 1143-1153.

Meester et al., "In Vivo Inhibition of Dipeptidyl Peptidase IV Activity by Pro-Pro-diphenyl-phosphonate (Prodipine)," Biochemical Pharmacology, 1997, vol. 54, pp. 173-179.

Mentlein et al., "Dipeptidyl-Peptidase Iv Hydrolyses Gastric Inhibitory Polypeptide, Glucagon-Like Peptide-1(7-36)amide, Peptide Histidine Methionine and is Responsible for their Degradation in Human Serum," European Journal of Biochemistry, 1993, vol. 214(3), pp. 829-835 (Abstract Only Provided).

Mesh, "Autoimmune Diseases," internet document www.ncbi.nlm.nih.gov/sites/entrez, accessed Oct. 31, 2007, 2 pages.

Michell et al., "Biomarkers and Parkinson's Disease," Brain, Aug. 2004, vol. 127, pp. 1693-1705.

Miller et al., "Peptide Inhibitor of Interleukin-8 (IL-8) Reduces Staphylococcal Enterotoxin-A (SEA) Induced Neutrophil Trafficking to the Lung," Inflamm. Res., 1996, vol. 45, pp. 393-397.

Milne, et al. "The biological activity of selected cyclic dipeptides," J. Pharm. Pharmacol., 1998, vol. 50, pp. 1331-1337.

Minelli et al., "Phosphoproteomic analysis of the effect of cyclo-[His-Pro] dipeptide on PC12 cells." Peptides, Jan. 2006;27(1):105-113. Epub Aug. 30, 2005 Abstract only PMID: 16137790.

Mitsuma et al., "Radioimmunoassay for Thyrotropin-Releasing Hormone Precursor Peptide, Lys-Arg-Gln-His-Pro-Gly-Arg-Arg," Exp Clin Endocrinology, 1989, vol. 93(1), pp. 53-60 (Abstract Only Provided).

Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds," Research Communications in Molecular Pathology and Pharmacology, 2002, vol. 111, pp. 199-209.

Mizuma et al., "Intestinal Absorption of Stable Cyclic Glycylphenylalanine: Comparison with the Linear Form," J. Pharm. Pharmacol., 1997, vol. 49, pp. 1067-1071.

Molodavkin et al., "[Effect of the novel dipeptide nootropic agent noopept and its metabolite cyclo-L-prolylglycine on the transcallosal evoked potential in the rat brain]," Eksp Klin Farmakol, Mar.-Apr. 2002, vol. 65(2) (Abstract Only Provided).

Monaco et al., "Plasma and cerebrospinal fluid tryptophan in Multiple Sclerosis and Degenerative Diseases," J Neurol Neurosurg Psychiatry, 1979, vol. 42(7), pp. 640-641 (Abstract Only Provided).

Montine et al., "Cerebrospinal Fluid Ab42, Tau, and F2-Isoprostane Concentrations in Patients with Alzheimer Disease, Other Dementias, and in Age-Matched Controls," Acrch Pathol Lab. Med, Apr. 2001, vol. 125, pp. 510-512.

Mori et al., "Alteration by Liquid Protein Diet of TRH and Cyclo(His-Pro) in the Young Rat Brain," Res. Commun Chem Pathol Pharmacol, 1985, vol. 47(1), pp. 157-160 (Abstract Only Provided).

(56) References Cited

OTHER PUBLICATIONS

Mori et al., "Brain TRH and Cyclo (His-Pro) and Brain Protein in the Newborn Rat are Altered by Maternal Liquid Protein Feeding," Life Sci, 1983, vol. 32(14), pp. 1607-1612 (Abstract Only Provided).

Mori et al., "Distribution of histidyl-proline diketopiperazine [cyclo (His-Pro)] and thyrotropin-releasing hormone (TRH) in the primate central nervous system," Brain Res, 1982, vol. 245(1), pp. 183-186.

Mori et al., "Histidyl-Proline Diketopiperazine Cyclo (His-Pro): Identification and Characterization in Rat Pancreatic Islets," Biochem Biophys Res Commun, 1983, vol. 115(1), pp. 281-286 (Abstract Only Provided).

Mori et al., "Histidyl-Proline Diketopiperazine cyclo (His-Pro): measurement by radioimmunoassay in human blood in normal subject and in patients with hyper- and hypothyroidism," Biochem Biophys Res Commun, 1982, vol. 109(2), pp. 541-547.

Mori et al., "Regional Dissociation of Histidyl-Proline Diketopiperazine (Cyclo-(His-Pro)) and Thyrotropin-Releasing Hormone (TRH) in the Rat Brain," Brain Research, 1982, vol. 231(2), pp. 451-453 (Abstract Only Provided).

Mori et al., "Specific Radioimmunoassay of Cyclo (His-Pro), a Biologically Active Metabolite of Thyrotropin-Releasing Hormone," Endocrinology, 1981, vol. 108(5), pp. 1995-1997 (Abstract Only Provided).

Mori et al., ["TRH and Cyclo (His-Pro) Concentrations in the Young Rat Brain are Altered by a Liquid Protein Diet]," [Article in Japanese], Nippon Naibunpi Gakkai Zasshi, 1987, vol. 63(7), pp. 846-852 (English Abstract Only).

Morley et al., "Neuropeptides and appetite: contribution of neuropharmacological modeling," Fed. Proc., Nov. 1984, vol. 43(14), pp. 2903-2907 (Abstract Only Provided).

Moss et al., "Kinetics and Mechanism of the Facile Cyclization of Histidyl-Prolineamide to Cyclo (His-Pro) in Aqueous Solution and the Competitive Influence of Human Plasma," J Pharm Pharmacol, 1990, vol. 42(1), pp. 7-12 (Abstract Only Provided).

Moss et al. "Th1/Th2 cells in inflammatory disease states: therapeutic implications," Expert Opinion on Biological Therapy, Dec. 2004, vol. 4, No. 12, pp. 1887-1896.

Murray et al., "Role of α-Synuclein Carboxy-Terminus on Fibril Formation in Vitro," Biochemistry, 2003, vol. 42, pp. 8530-8540.

Nakamura et al., "T-cell mediated inflammatory pathway in osteoarthritis," Osteoarthritis & Cartilage, 1999, vol. 7, pp. 401-402.

Neustadt, "Intra-articular injections for osteoarthritis of the knee," Cleveland Clinic J. Med., 2006, vol. 73(10), pp. 897-911.

Nicholson et al., "NPI-2358 is a tubulin-depolymerizing agent: in-vitro evidence for activity as a tumor vascular-disrupting agent," Anticancer Drugs, Jan. 2006, vol. 17(1), pp. 25-31 (Abstract Only Provided).

Nitecki et al., "A Simple Route to Sterically Pure Kiketopiperazines" J. Org. Chem., 1968, vol. 33(2), pp. 864-866.

O'Connor et al., "Post-proline dipeptidyl-aminopeptidase from synaptosomal membranes of guinea-pig brain," European Journal of Biochemistry, 1986, vol. 154, Iss. 2, pp. 329-335.

Ostrovskaia et al., "Multicomponent antithrombotic effect of the neuroprotective prolyl dipeptide GVS-111 and its major metabolite cyclo-L-prolylglycine," Eksp Klin Farmakol, Mar.-Apr. 2002, vol. 65(2) (Abstract Only Provided).

Palace et al. "Epilepsy: an autoimmune disease?" Journal of Neurology, Neurosurgery & Psychiatry, Dec. 2000, vol. 69, No. 6, pp. 711-714.

Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells," Clin. Exp. Immunol., 1998, vol. 111, pp. 588-596.

Pandey et al., "Synthetic Peptides Corresponding to a Repetitive Sequence of Malarial Histidine Rich Protein Bind Haem and Inhibit Haemozoin Formation in vitro," Mol Biochem Parasitol, 1997, vol. 90(1), pp. 281-287 (Abstract Only Provided).

Parker et al., "Evidence for the Presence of Immunoreactive Histidyl-Proline Diketopiperazine [Cyclo (His-Pro)] in the Adult Human Brain," Peptides, Nov.-Dec. 1983, vol. 4(6), pp. 879-881 (Abstract Only Provided).

Pekary et al., "In vitro Production of a TRH-Homologous Peptide and His-Pro Diketopiperazine by Human Semen," J Androl, 1985, vol. 6(6), pp. 379-385 (Abstract Only Provided).

Prakash et al., "Synthesis and Biological Activity of Novel Neuroprotective Diketopiperazines," Bioorganic & Medicinal Chemistry, Sep. 2002, vol. 10(9), pp. 3043-3048.

Prasad, "Bioactive Cyclic Dipeptides," Peptides, 1995, vol. 16(1), pp. 151-164.

Prasad et al., "Distribution and Characterization of Cyclo (His-Pro)-Like Immunoreactivity in Human Cerebrospinal Fluid," Biochem Biophys Res Commun, 1986, vol. 136(2), pp. 835-842 (Abstract Only Provided).

Prasad et al., "Distribution and Metabolism of Cyclo (His-Pro): A New Member of the Neuropeptide Family," Peptides, May-Jun. 1982, vol. 3(3), pp. 591-598 (Abstract Only Provided).

Prasad et al., "Increased cerebrospinal fluid cyclo(His-Pro) content in schizophrenia," Neuropeptides, Nov. 1991, vol. 20(3), pp. 187-190.

Prasad et al., "Isolation of cyclo(His-Pro)-like immunoreactivity from Human Urine and Demonstration of its Immunologic, Pharmacologic, and Physico-chemical Identity with the Synthetic Peptide," Biochemistry Int, 1990, vol. 21(3), pp. 425-434 (Abstract Only Provided).

Prasad et al., "Thermoregulation in rats: opposing effects of thyrotropin releasing hormone and its metabolite histidyl-proline diketopiperazine," Biochem Biophys Res. Commun., 1978, vol. 85(4), pp. 1582-1587.

Purves et al., Life: the Science of Biology, 3rd Ed. (1992), p. 376.

Purves et al. (Eds), Neuroscience, 2001, Sinauer Associates, Inc., 2nd Edition, pp. 75, 367, 400 and 403.

Rainbow et al., "Distribution, survival and biological effects in mice of a behaviorally active, enzymatically stable peptide: pharmacokinetics of cyclo(Leu-Gly) and puromycin-induced amnesia," Pharmacol Biochem Behav, May 1979, vol. 10(5), pp. 787-793.

Rainger et al., "Endothelial-Borne Platelet-Activating Factor and Interleukin-8 Rapidly Immobilize Rolling Neutrophils," Am. J. Physiol., 272(Heart Circ. Physiol. 41):H114-H122 (1997).

Rainsford et al., "Effects of 5-Lipoxygenase Inhibitors on Interleukin Production by Human Synovial Tissues in Organ Culture: Comparison with Interleukin-1-Synthesis Inhibitors," J. Pharm. Pharmacol., 48:46-52 (1996).

Ramírez et al., "Platelet Activating Factor Modulates Microvascular Permeability through Nitric Oxide Synthesis," Microvascular Research, 1995, vol. 50, Iss. 2, pp. 223-234.

Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," J Pharm Biomed Anal 1999, 19(3-4):2.

Rinaldi et al. "Immunological markers in multiple sclerosis: tackling the missing elements," Neurol. Sci., Dec. 2005, vol. 26 Suppl. 4, pp. S215-S217.

Rosenthal et al., "Effects of Arachidonic Acid and Cyclo (His-Pro) on Zinc Transport Across Small Intestine and Muscle Tissues," Life Sci, 2001, vol. 70(3), pp. 337-348 (Abstract Only Provided).

Roth et al., "Platelet-Activating Factor Exerts Mitogenic Activity and Stimulates Expression of Interleukin 6 and Interleukin 8 in Human Lung Fibroblasts via Binding to its Functional Receptor," J. Exp. Med., 1996, vol. 184, pp. 191-201.

Sakurada et al., "Antinociceptive activities of synthetic dipeptides in mice." J. Pharm. Pharmacol., 1982, vol. 34, pp. 750-751.

Sakuta et al., "Dual Regulatory Effects of Interferon-α, -β, and -γ on Interleukin-8 Gene Expression by Human Gingival Fibroblasts in Culture Upon Stimulation with Lipopolysaccharide from *Prevotella intermedia,* Interleukin-1α, or Tumor Necrosis Factor-α," J. Dent Res., 1998, vol. 77(8), pp. 1597-1605.

Samanta et al., "Crystal Structure of Human Plasma Platelet-activating Factor Acetylhydrolase," J. Biol. Chem., vol. 283(46), Nov. 14, 2008, pp. 31617-31624.

(56) References Cited

OTHER PUBLICATIONS

Sammes, "Naturally Occurring 2,5-Dioxopiperazines and Related Compounds," Fortschr. Chem. Org. Naturst., 1975, vol. 32, pp. 51-118.

Sano et al. "Process Research and Development of L-Alanyl-L-Glutamine, a Component of Parenteral Nutrition," Organic Process Research & Development, 2000, vol. 4, pp. 147-152.

Sato et al., "Comparison of the antiociceptive effect between the cyclic dipeptide cyclo[Tyr(Et)-homoarginine] and the linear dipeptide Boc-Tyr(Et)-homoarginine-Ome in rats.," Jpn J Pharmacol, Jan. 1984, vol. 34(1) (Abstract Only Provided).

Scharpe et al., "Peptide Truncation by Dipeptidyl Peptidase IV: A New Pathway for Drug Discovery," Verh K. Acad Geneeskd Belg. 2001, vol. 63(1), pp. 5-32 (Abstract Only Provided).

Schlingemann et al., "Role of vascular permeability factor/vascular endothelial growth factor in eye disease," Brit. J. Ophthalmology, vol. 81, 1997, pp. 501-512.

Seredenin et al. " Endogenous dipeptide cycloprolylglycine shows selective anxiolytic activity in animals with manifest fear reaction," Bull Exp Biol Med; Apr. 2002; vol. 1333(4) (Abstract Only Provided).

Sepetov et al., "Rearrangement, Racemization and Decomposition of Peptides in Aqueous Solution," Peptide Research, 1991, vol. 4(5), pp. 308-313 (Abstract Only Provided).

Shaw et al., "Future of early detection of lung cancer: the role of mouse models." Clin Cancer Res., Jul. 1; 11(13 Pt 2): 4999s-5003s, 2005.

Shimizaki et al., "Diketopiperazine Derivatives, a New Series of Platelet-Activating Factor Inhibitors," Chem. Pharm. Bull., 1987, vol. 35(8), pp. 3527-3530.

Shimazaki et al., "Diketopiperazines as a New Class of Platelet-Activating Factor Inhibitors," J. Med. Chem., 1987, vol. 30, pp. 1706-1709.

Shimazaki et al., "PAF Inhibitory Activity of Diketopiperazines: Structure-Activity Relationships," Lipids, 1991, vol. 26(12), pp. 1175-1178.

Shimi et al., "Isolation of Cairomycins A and C," Antimicrobial Agents and Chemotherapy, Jun. 1981, vol. 19(6), pp. 941-944.

Shukla et al., "Role of Endogenous Cyclo(His-Pro) in Cold-Induced Hypothermia in the Desert Rat (*Mastomys natalensis*)," Peptides; 1994; 15(8):1471-4 (Abstract Only Provided).

Shutov et al., "[Diagnostic Significance of the type of In Vitro Interaction between Blood Lymphocytes and Serotonin in Multiple Sclerosis]," [Article in Russian], Zh Nevrol Psikhiatr Im S S Korsakova, 2002, vol. 102(4), pp. 35-38 (Abstract Only Provided).

Skates et al., "Molecular markers for early detection of renal carcinoma: investigative approach," Clin Cancer Res, Sep. 2004, vol. 10(18 Pt 2), pp. 6296S-6301S.

Smith et al., "Lesson 10, vol. 12—Asthma: Evolving Anti-Inflammatory Therapy," www.chestnetorg/education/pccu/vol12/lesson10.html, pp. 1-8, printed Jul. 20, 2000.

Smith et al., "Recent developments in drug therapy for multiple sclerosis," Mult. Scler., 1999, vol. 5, pp. 110-120.

Smith et al., "Solid-phase synthesis of a library of piperazinediones and diazepinediones via Kaiser oxime resin." Bioorg. Med. Chem., 1998, vol. 8, pp. 2369-2374.

Sollid et al. "Is celiac disease an autoimmune disorder?" Current Opinion in Immunology, Dec. 2005, vol. 17, No. 6, pp. 595-600.

Sollis "Short and novel stereospecific synthesis of trisubstituted 2,5-diketopiperazines," J Org Chem, Jun. 2005, vol. 70(12), pp. 4735-4740 (Abstract Only Provided).

Song et al., "Raw vegetable food containing high cyclo (his-pro) improved insulin sensitivity and body weight control," Metabolism, Nov. 2005, vol. 54(11), pp. 1480-1489 (Abstract Only Provided).

Song et al., "Synergistic Antidiabetic Activities of Zinc, Cyclo (His-Pro), and Arachidonic Acid," Metabolism 2001 50(1):53-59 (Abstract Only Provided).

Stark et al., "Structures, sensory activity, and dose/response functions of 2,5-diketopiperazines in roasted cocoa nibs (*Theobroma cacao*)." J Agric Food Chem., Sep. 7, 2005, vol. 53(18), pp. 7222-7231 (Abstract Only Provided) PMID: 16131134.

Steiner et al., "Histidyl Proline Diketopiperazine (Cyclo [His-Pro]) in Eating Disorders," Neuropeptides, Oct. 1989, vol. 14(3), pp. 185-189 (Abstract Only Provided).

Strom et al., "*Lactobacillus plantarum* MiLAB 393 produces the antifungal cyclic dipeptides cyclo(L-Phe-L-Pro) and cyclo(L-Phe-trans-4-Oh-L-Pro) and 3-phenyllactic acid.," Appl Environ Microbiol, Sep. 2002, vol. 68(9) (Abstract Only Provided).

Suzuki et al., "Effect of cyclic dipeptides containing histidine on pentobarbital narcosis," J. Pharm. Dyn., May 1981, vol. 4(5), pp. 377-379.

Takahara et al., "Detection in Human Serum by Radioimmunoassay of Histidyl-Proline Diketopiperazine, a Metabolite of Thyrotropin-Releasing Hormone," J Clinical Endocrinology, 1983, vol. 56(2), pp. 312-319 (Abstract Only Provided).

't Hart et al., "Evaluating the validity of animal models for research into therapies for immune-based disorders," DDT, 2004, vol. 9(12), pp. 517-524.

Tascioglu et al., "Efficacy of intra-articular sodium hyaluronate in the treatment of knee osteoarthritis," Clinical Rheumatology, 2003, vol. 22, Iss. 2, pp. 112-117.

Teitel et al., "Rheumatoid arthritis," PubMed Health, reviewed Feb. 2, 2012, available at www.ncbi.nlm.nih.gov/pubmedhealth/PMH0001467/?report=printable, 8 pages.

Teitel et al., "Scleroderma," PubMed Health, reviewed Feb. 2, 2012, available at www.ncbi.nlm.nih.gov/pubmedhealth/PMH0001465/?report=printable, 7 pages.

Teitel et al., "Systemic lupus erythematosus," PubMed Health, reviewed Feb. 2, 2012, available at www.ncbi.nlm.nih.gov/pubmedhealth/PMH0001471/?report=printable, 9 pages.

Unal et al., "Cyclo(Gly-Gln) inhibits the cardiorespiratory depression produced by beta-endorphin and morphine," Brain Research, 1997, vol. 747(1), pp. 52-59.

Vara et al., "PI3K/Akt signalling pathway and cancer," Cancer Treatment Reviews, 2004, vol. 30, pp. 193-204.

Varughese et al., "Crystal structure and conformation of cyclo-L-cystine," Int. J. Pept. Protein Res., vol. 18, Jul. 1981, pp. 88-102.

Vogel et al., "Disseminated tumor cells—Their detection and significance for prognosis of gastrointestinal and pancreatic carcinomas," Virchows Arch, 2001, vol. 439, pp. 109-117.

Walter et al., "Neurohypophyseal hormones, analogs, and fragments: their effect on puromycin-induced amnesia," Proc. Natl. Acad. Sci., Oct. 1975, vol. 72(10), pp. 4180-4184.

Walter et al., "The Cyclized C-Terminal Dipeptide of Arginine Vasopressin: Metabolic Stability and Antagonism of Puromycin-Induced Amnesia," Hormones and Behavior, 1982, vol. 16; p. 234-244.

Wang et al., "A facile pathway to synthesize diketopiperazine derivatives," Tetrahedron Lett, 2002, vol. 43, pp. 865-867.

Wang et al., "Novel inhibitors of plasminogen activator inhibitor-1: development of new templates from diketopiperazines," Bioorg Med Chem Lett, Sep. 2002, vol. 12(17), pp. 2367-2370 (Abstract Only Provided).

Weng et al., " Novel CCK-B receptor agonists: diketopiperazine analogues derived for CCK4 bioactive conformation," Regul Pept, Aug. 1996; vol. 65(1) (Abstract Only Provided).

Wennemers et al., "Diketopiperazine Receptors: A Novel Class of Highly Selective Receptors for Binding Small Peptides," Chem. Eur. J., 2001, vol. 7, No. 15, pp. 3342-3347.

Wilber et al., "Endogenous histidyl-proline diketopiperazine [cyclo (His-Pro)]: a potential satiety neuropeptide in normal and genetically obese rodents," Trans Assoc Am Physicians, 1983, vol. 96, pp. 131-136.

Wilber et al., "Histidyl-proline diketopiperazine: a potent and chronic appetite-inhibiting neuropeptide," Trans Assoc. Am Physicians, 1986, vol. 99, pp. 245-249.

Wilkes et al. "Patient Survival after Human Albumin Administration: A Meta-Analysis of Randomized, Controlled Trials." Annals of Internal Medicine, Aug. 2001, vol. 135, No. 3, pp. 149-164.

Wisniewski et al., "Relationship between serum cyclo (His-Pro) concentrations and the nutritional status of HIV-infected patients," South Med. J., Mar. 1994, vol. 87(3), pp. 348-351 (Abstract Only Provided).

(56) References Cited

OTHER PUBLICATIONS

Woehlecke et al., "Reversal of breast cancer resistance protein-mediated drug resistance by tryprostatin A.," Int J Cancer; Dec. 2003, vol. 107(5) (Abstract Only Provided).
Wolf et al., "Identification of Cyclo(His-Pro)-Like Immunoreactivity in Human Follicular Fluid: Correlation with Steroid and Peptide Hormones," J Soc Gynecol Investigation, 1994, vol. 1(3), pp. 220-224 (Abstract Only Provided).
Wretlind, "The Availability of the Isopropyl Ester of L- and D-Phenylalanine and 3,6-Dibenzyl- 2,5-Diketopiperazine form Growth in Rats," Acta phys. Scandinav, May 1953, vol. 30, pp. 97-104.
Wyatt et al., "2,5-Diketopiperazines as potent and selective oxytocin antagonists 1: Identification, stereochemistry and initial SAR," Bioorg Med Chem Lett., May 16 2005, vol. 15(10), pp. 2579-2582 (Abstract Only Provided) PMID: 15863320.
Yamada et al., "Abundance of Cyclo (His-Pro)-like Immunoreactivity in the Brain of TRH-Deficient Mice," Endocrinology, Jan. 1999, vol. 140(1), pp. 538-541 (Abstract Only Provided).
Yanagisawa et al., "The Subcellular and Organ Distribution and Natural Form of Histidyl-Proline Diketopiperazine in Rat Brain Determined by a Specific Radioimmunoassay," J Biol Chem, Nov. 10, 1980, vol. 255(21), pp. 10290-10294 (Abstract Only Provided).
Yang et al. "Increased hepatic platelet activating factor (PAF) and PAf receptors in carbon tetrachloride induced liver cirrhosis." Gut, Jan. 2004, vol. 53, No. 6, pp. 877-883.
Yi Es, "Hypersensitivity pneumonitis," Crit Rev Clin Lab Sci., Nov. 2002, vol. 39(6), pp. 581-629.
Yoshida et al., "PAF Inhibitors of Microbial Origin," Prog. Biochem. Pharmacol., 1988, vol. 22, pp. 68-80.
Youngblood et al., "Bovine Serum Albumin-GABA-His-Pro-NH2: an Immunogen for Production of Higher Affinity Antisera for TRH," J Neursci Methods, 1983, vol. 9(4), pp. 367-373 (Abstract Only Provided).
Zeng et al., "Synthesis of a small library of diketopiperazines as potential inhibitors of calpain," Bioorg Med Chem Lett, Jun. 2005, vol. 15(12), pp. 3034-8.
Zieve, "Multiple sclerosis," PubMed Health, reviewed Sep. 26, 2011, available at www.ncbi.nlm.nih.gov/pubmedhealth/PMH0001747/?report=printable, 10 pages.
Official Action for Australian Patent Application No. 2001279313, mailed Jun. 29, 2005.
Official Action for Brazilian Patent Application No. PI-0112969-4, published May 25, 2010.
Official Action (with English translation) for Brazilian Patent Application No. PI-0112969-4, dated Jul. 16, 2013, 10 pages.
Official Action for Canadian Patent Application No. 2,417,960, mailed Jan. 25, 2008.
Official Action for Canadian Patent Application No. 2,417,960, mailed Sep. 22, 2009.
Official Action for Canadian Patent Application No. 2,417,960, dated Jul. 7, 2010.
Official Action for Canadian Patent Application No. 2,417,960, dated Feb. 23, 2011.
Notice of Allowance for Canadian Patent Application No. 2,417,960, dated Oct. 20, 2011.
Official Action for Canada Patent Application No. 2,774,959, dated Jul. 13, 2012, 4 pages.
Translation of the First Official action for Chinese Patent Application No. 018158374, mailed Jan. 21, 2005.
Translation of the Second Official action for Chinese Patent Application No. 018158374, mailed May 23, 2008.
Translation of the Third Official action for Chinese Patent Application No. 018158374, mailed Oct. 31, 2008.
Translation of the Fourth Official action for Chinese Patent Application No. 018158374, mailed Apr. 3, 2009.
English Translation of First Office Action for Chinese Patent Application No. 200910145682.4, dated Apr. 13, 2010.
Official Action (translation only) for Chinese Patent Application No. 200910145682.4, issued Oct. 9, 2010.
Examination Report for European Patent Application No. 01957581.0, mailed Mar. 30, 2006.
Examination Report for European Patent Application No. 01957581.0, mailed Sep. 14, 2007.
Official Action for European Patent Application No. 01957581.0, mailed Apr. 8, 2009.
Official Action for European Patent Application No. 01957581.0, mailed Mar. 2, 2010.
Official Action (translation only) for Japanese Patent Application No. 2002-517014, dated Dec. 6, 2011.
Official Action (with English translation) for Japanese Patent Application No. 2012-129131, mailed Aug. 13, 2013, 4 pages.
International Search Report for International (PCT) Patent Application No. PCT/US01/41541, mailed Feb. 19, 2002.
Written Opinion for International (PCT) Patent Application No. PCT/US01/41541, mailed Sep. 5, 2002.
International Preliminary Examination Report for International (PCT) Patent Application No. PCT/US01/41541, completed Oct. 10, 2002.
Morely et al., "Histidyl-proline diketopiperazine decreases food intake in rats," Brain Research, 1981, vol. 210, Iss. 1-2, pp. 475-478.
Official Action for Canada Patent Application No. 2,774,959, dated Nov. 6, 2013, 3 pages.
Brown et al., "Anti-VEGF Agents in the Treatment of Neovascular Age-related Macular Degeneration: Applying Clinical Trial Results to the Treatment of Everyday Patients," American Journal of Opthalmology, 2007, vol. 144, Iss. 4, pp. 627-637.
Hollyfield et al., "Oxidative damage-induced inflammation initiates age-related macular degeneration," Nature Medicine, 2008, vol. 14, No. 2, pp. 194-198.
Kullenberg et al., "Intraarticular Corticosteroid Injection: Pain Relief in Osteoarthritis of the Hip?," Journal of Rheumatology, 2004, vol. 31, No. 11, pp. 2265-2268.
Lewis et al., "Hydrogen Peroxide Stimulates the Synthesis of Platelet-activating Factor by Endothelium and Induces Endothelial Cell-dependent Neutrophil Adhesion," The Journal of Clinical Investigation, 1988, vol. 82, Iss. 6, pp. 2045-2055.
Ma et al., "Platelet-Activating Factor (PAF) Induces Corneal Neovascularization and Upregulates VEGF Expression in Endothelial Cells," Investigative Ophthalmology & Visual Science, 2004, vol. 45, No. 9, pp. 2915-2921.
Nicolson, "Metabolic syndrome and mitochondrial function: Molecular replacement and antioxidant supplements to prevent membrane peroxidation and restore mitochondrial function," Journal of Cellular Biochemistry, 2007, vol. 100, Iss. 6, pp. 1352-1369.
Otani et al., "Bone marrow-derived stem cells target retinal astrocytes and can promote or inhibit retinal angiogenesis," Nature Medicine, 2002, vol. 8, No. 9, pp. 1004-1010.
Oztuna et al., "Intra-articular Injection of Tenoxicam in Osteoarthritic Knee Joints With Effusion," Orthopedics, 2007, vol. 30, Iss. 12, pp. 1039-1042.
Watterson et al., "Viscosupplementation: Therapeutic Mechanisms and Clinical Potential in Osteoarthritis of the Knee," Journal of the American Academy of Orthopaedic Surgeons, 2000, vol. 8, No. 5, pp. 277-284. Abstract Only.
Chan, "Chapter 9: Transplant Rejection and Its Treatment," Atlas of Diseases of the Kidney, vol. 5, (Ed.Henrich et al.), Wiley-Blackwell, 1999, pp. 9.1-9.13.
Horwitz et al., "Piperazinedione plus total body irradiation: an alternative preparative regimen for allogeneic bone marrow transplantation in advanced phases of chronic myelogenous leukemia," Bone Marrow Transplantation, 1989, vol. 4, Iss. 1, pp. 101-105.
Zander et al., "Allogeneic bone marrow transplantation for acute leukemia refractory to induction chemotherapy," Cancer, 1985, vol. 56, Iss. 6, pp. 1374-1379.

* cited by examiner

METHOD OF USING DIKETOPIPERAZINES AND COMPOSITION CONTAINING THEM

This application is a continuation of U.S. application Ser. No. 13/252,377, filed Oct. 4, 2011, which is a continuation of U.S. application Ser. No. 10/397,964, filed Mar. 25, 2003, now U.S. Pat. No. 8,455,517, which is a continuation of issued U.S. Pat. No. 6,555,543, filed Aug. 2, 2001 and issued Apr. 29, 2003, which claims benefit of provisional application 60/222,849, filed Aug. 4, 2000. The entire disclosure of the prior applications, are hereby incorporated by reference.

FIELD OF THE INVENTION

This invention relates to methods of inhibiting the effects of platelet activating factor using certain diketopiperazines. The invention also relates to methods of inhibiting the production and/or release of interleukin 8 (IL-8) using these diketopiperazines. Finally, the invention relates to pharmaceutical compositions comprising the diketopiperazines.

BACKGROUND

Platelet activating factor (PAF; 1-O-alkyl-2-acetyl-sn-glycerol-3-phosphorylcholine) is a potent inflammatory phospholipid mediator with a wide variety of biological activities. It is generated and released by basophils, monocytes, macrophages, polymorphonuclear leukocytes, eosinophils, neutrophils, natural killer lymphocytes, platelets and endothelial cells, as well as by renal and cardiac tissues under appropriate immunological and non-immunological stimulation. See PCT application WO 94/04537. PAF mediates biological responses by binding to specific PAF receptors found in a wide variety of cells and tissues. Structure-activity studies on PAF and its analogs indicate that the ability of PAF to bind to these receptors is structure specific and stereospecific. See PCT WO 94/04537.

While PAF mediates essential biological responses, it also appears to play a role in pathological immune and inflammatory responses. Many published studies have provided evidence for the involvement of PAF in diseases, including arthritis, acute inflammation, asthma, allergic reactions, cardiovascular diseases, neoplastic diseases, endotoxic shock, pain, psoriasis, ophthalmic inflammation, ischemia, gastrointestinal ulceration, myocardial infarction, inflammatory bowel diseases, and acute respiratory distress syndrome. See PCT application WO 94/04537.

The involvement of PAF in pathological inflammatory and immune states has stimulated a substantial research effort to identify PAF receptor antagonists, and a number of compounds of diverse chemical structure have been identified as PAF antagonists. See, e.g., PCT applications WO 94/04537 and WO 96/00212 (and references cited in these two applications), PCT applications WO 95/18610 and WO 99/49865, U.S. Pat. Nos. 4,940,709, 5,358,938, 5,434,151, 5,463,083, 5,648,486, 5,741,8095,792,776, 5,780,503, 5,856,323, Japanese application 63 290868, Shimazaki et al., *Chem. Pharm. Bull.*, 35(8), 3527-3530 (1987), Shimazaki et al., *J. Med. Chem.*, 30, 1709-1711 (1987), Yoshida et al., *Prog. Biochem. Pharmacol.*, 22, 68-80 (1988), Shimazaki et al., *Lipids*, 26(12), 1175-1178 (1991). Given the significant number of pathological immune and inflammatory responses that are mediated by PAF, there remains a need to identify new compounds and compositions that inhibit PAF activity.

Diketopiperazines have been reported to exhibit a variety of biological activities. See, e.g., U.S. Pat. No. 4,289,759 (immunoregulatory agents), U.S. Pat. No. 4,331,595 (immunoregulatory agents), U.S. Pat. No. 4,940,709 (PAF antagonists), U.S. Pat. No. 5,700,804 (inhibitors of plasminogen activator inhibitor), U.S. Pat. No. 5,750,530 (inhibitors of plasminogen activator inhibitor), U.S. Pat. No. 5,990,112 (inhibitors of metalloproteases), PCT applications WO 97/36888 (inhibitors of farnesyl-protein transferase) and WO 99/40931 (treatment of central nervous system injury), EP application 43219 (immunoregulatory agents), Japanese application 63 290868 (PAF antagonists), Japanese application 31 76478 (immunosuppressive agents), Shimazaki et al., *Chem. Pharm. Bull.*, 35(8), 3527-3530 (1987) (PAF antagonists), Shimazaki et al., *J. Med. Chem.*, 30, 1709-1711 (1987) (PAF antagonists), Shimazaki et al., *Lipids*, 26(12), 1175-1178 (1991) (PAF antagonists), Yoshida et al., *Prog. Biochem. Pharmacol.*, 22, 68-80 (1988) (PAF antagonists), Alvarez et al., *J. Antibiotics*, 47(11), 1195-1201 (1994) (inhibitors of calpain)

The diketopiperazine composed of aspartic acid and alanine (3-methyl-2,5-diketopiperazine-6-acetic acid; DA-DKP) is known. It has been reported to be formed as a result of the degradation of human albumin stored above 30° C. Chan et al., *Eur. J. Biochem.*, 227, 524-528 (1995). It is not known to have biological activity.

SUMMARY OF THE INVENTION

The invention provides a method of treating a disease or condition mediated by platelet activating factor. The method comprises administering to an animal in need thereof an effective amount of a diketopiperazine of the formula:

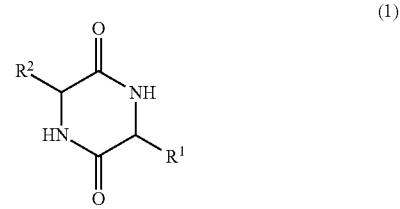

(1)

wherein:
R$^1$ is —CH$_2$COR$^3$, or —CH$_2$CH$_2$COR$^3$;
R$^2$ is the side chain of an amino acid selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine;
R$^3$ is —OH, —NH$_2$—OR$^4$, —NHR$^4$, or —NR$^4$R$^4$; and
each R$^4$ is independently an alkyl, aryl, alkylaryl, or arylalkyl; or
a physiologically-acceptable salt thereof.

The invention further provides a method of inhibiting inflammation. The method comprises administering to an animal in need thereof an effective amount of a compound of formula (1) or a physiologically-acceptable salt thereof.

The invention also provides a method of inhibiting aggregation of platelets. The method comprises contacting the platelets with an effective amount of a compound of formula (1) or a physiologically-acceptable salt thereof.

In addition, the invention provides a method of inhibiting the production, release or both of interleukin 8 by cells. The method comprises contacting the cells with an effective amount of a compound of formula (1) or a physiologically-acceptable salt thereof.

The invention further provides a method of inhibiting the effects of platelet activating factor (PAF). The method comprises contacting the PAF with an effective amount of a compound of formula (1) or a physiologically-acceptable salt thereof.

Finally, the invention provides a pharmaceutical composition. The composition comprises a pharmaceutically-acceptable carrier and a compound of formula (1) or a physiologically-acceptable salt thereof.

DETAILED DESCRIPTION OF THE PRESENTLY-PREFERRED EMBODIMENTS

By "side chain" of an amino acid is meant that portion of the amino acid attached to the common

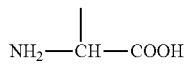

backbone of all of the amino acids listed above. For instance, the side chain of glycine is —H, the side chain of alanine is —CH$_3$, and the side chain of serine is —CH$_2$OH.

By "alkyl" is meant a straight-chain or branched-chain alkyl containing 1-30 carbon atoms, preferably 1-18 carbon atoms. "Lower alkyl" means a straight-chain or branched chain alkyl containing 1-6 carbon atoms.

By "aryl" is meant an aromatic group having at least one aromatic ring (e.g., phenyl).

By "alkylaryl" is meant a lower alkyl having an aryl having attached thereto (e.g., —CH$_2$C$_6$H$_5$ or —CH$_3$CH(C$_6$H$_5$)CH$_3$).

By "arylalkyl" is meant an aryl having a lower alkyl having attached thereto (e.g., —C$_6$H$_4$—CH$_3$).

"Inhibit" is used herein to mean to reduce (wholly or partially) or to prevent.

"Mediated" is used herein to mean caused by, exacerbated by, or involving.

"Treat" is used herein to mean to reduce (wholly or partially) the symptoms of a disease or condition, including curing the disease or condition, or to prevent the disease or condition.

The present invention is based on the discovery that 3-methyl-2,5-diketopiperazine-6-acetic acid (DA-DKP) inhibits PAF activity. This inhibition appears to be due to the binding of DA-DKP to both PAF and PAF receptors. It is believed that the binding of DA-DKP to PAF is due to ion pairing of the carboxyl of DA-DKP with N$^+$ on the choline portion of PAF. Thus, other diketopiperazines comprising one or more carboxyls would be expected to be effective inhibitors of PAF. Indeed, it is possible that other non-diketopiperazine compounds comprising carboxyls, such as poly-aspartic acid or poly-glutamic acid, would also be effective inhibitors of PAF. The mechanism by which DA-DKP binds to PAF receptors is not known, but it is hypothesized to be due to the diketopiperazine ring structure of the DA-DKP and/or the hydrophobic R$^2$ side chain of DA-DKP.

Methods of preparing diketopiperazines are known in the art, and these methods may possibly be employed to synthesize the diketopiperazines of formula (1). See, e.g., U.S. Pat. Nos. 4,694,081 and 5,817,751; Smith et al., *Bioorg. Med. Chem. Letters*, 8, 2369-2374 (1998). However, difficulties may be encountered or unsatisfactory results may be obtained when using prior art methods to synthesize diketopiperazines of formula (1) (see co-pending provisional application 60/223,075, filed on Aug. 4, 2000). Accordingly, it is highly preferable that the diketopiperazines of formula (1) be synthesized as described in co-pending provisional application 60/223,075, the complete disclosure of which is incorporated herein by reference.

The synthesis described in provisional application 60/223,075 utilizes standard solution-phase or solid-phase peptide synthetic methods which are well known in the art. Solid-phase peptide synthetic methods are preferred.

The first step of the synthesis described in provisional application 60/223,075 comprises providing a first amino acid. The first amino acid is selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine. These amino acids, which may be in their D- or L-enantiomeric form, are commercially available or can be made by methods well known in the art (see, e.g., Williams, *Synthesis Of Optically Active α-Amino Acids* (Pergammon Press, 1989)). Preferred are hydrophobic amino acids such as glycine, alanine, valine, leucine, isoleucine, and phenylalanine. Particularly preferred is alanine.

The first amino acid is also preferably protected with one or more protecting groups to prevent unwanted side reactions during the synthesis. Such protecting groups, and methods for attaching and removing them, are well known in the art. See, e.g., Green and Wuts, *Protective Groups In Organic Chemistry* (Wiley 1992) and Grant, *Synthetic Peptides: A User's Guide* (Freemen 1992).

The first amino acid is reacted with an aspartic acid derivative of the following formula NH$_2$CH(CH$_2$COOR$^5$)COOH or a glutamic acid derivative of the following formula NH$_2$CH(CH$_2$CH$_2$COOR$^5$)COOH, wherein R$^5$ is a lower alkyl or alkylaryl. Preferably R$^5$ is benzyl (—CH$_2$C$_6$H$_5$; Bz). The benzyl group has been found not only to protect the side-chain carboxyls of these amino acids, but also to facilitate cyclization of the dipeptide. Furthermore, the benzyl can be removed from the dipeptide under neutral conditions which prevents racemization of the chiral center (carbons bearing the R$^1$ and R$^2$ groups).

The aspartic and glutamic acid derivatives NH$_2$CH(CH$_2$COOR$^5$)COOH and NH$_2$CH(CH$_2$CH$_2$COOR$^5$)COOH are commercially available or may be prepared by known methods (see, e.g., Bodansky and Bodansky, *The Practice of Peptide Synthesis*, pages 63-66 (2nd ed., Springer-Verlag, 1994). The amino group or α carboxyl group of the aspartic and glutamic acid derivatives can optionally be blocked with a standard protecting group (see above) in order to prevent unwanted side reactions.

As noted above, the synthesis of the diketopiperazines preferably utilizes solid-phase peptide synthetic methods. The first amino acid or the aspartic or glutamic acid derivative is attached to a solid support through its α carboxyl for solid-phase synthesis. The solid support may be any solid support which is compatible with peptide synthesis, such as those described in Grant and Atherton, *Solid Phase Peptide Synthesis: A Practical Approach* (IRL Press 1989). Suitable solid supports are available commercially or can be prepared by standard methods. See PCT application WO 96/00391. The solid support may contain linker or spacer molecules which anchor the first amino acid or the aspartic acid or glutamic acid derivative to the support surface. A variety of linkers with different properties are well known in the art. See, e.g., Grant, *Synthetic Peptides: A User's Guide* (Freemen 1992) and PCT application WO 96/00391. The linker will typically include a functional group to which the first amino acid or the aspartic acid or glutamic acid derivative is attached.

Preferably, the first amino acid is attached to the solid support and, prior to coupling the aspartic acid or glutamic acid derivative to the first amino acid, the protecting group, if present, on the α amino group of the bound first amino acid is removed. The removal of the protecting group of any side-chain amino groups should be avoided, however, so conditions must be chosen to deprotect the α amino group without deprotecting the side chain amino groups. Suitable deprotection conditions are known in the art. For example, removal of 9-fluorenylmethyloxycarbonyl may be performed with 20% to 55% of a secondary amine base, such as piperidine, in a polar, aprotic solvent, such as dimethylformamide, methylene chloride or N-methylpyrrolidine. Diisopropyl silane is preferably added to prevent transesterification during deprotection, which can be pronounced in large scale preparations.

The reaction between the first amino acid and the aspartic or glutamic acid derivative takes place under conditions effective to produce a peptide bond so that a dipeptide is formed. These conditions are well known in the art. For instance, a coupling catalyst (such as 2-(1H-benzotriazole-1-yl)-1,2,3,3-tetramethyluroniumtetrafluoroborate, benzotriazole-1-yl-oxytris(dimethylamino)phosphonium hexafluorophospate, 2-(1H-benzotriazole-1-yl)-1,1,3,3-tetramethyluroniumhexaphosphate, 1-hydroxybenzotriazole, diisopropylamine, dicyclohexylcarbodiimide), may be used to effect formation of the dipeptide. Typically, an excess of the coupling catalyst is used, with quantities ranging from 2 to 10 equivalents or more. Often the degree of excess is determined with respect to the reactivity of the chemical species being coupled. Polar, aprotic solvents (such as dimethylformamide, N-methylpyrrollidine, methylene chloride and dimethylsulfoxide) are preferred. Reaction times may vary from one-half hour to overnight, and temperatures may vary from room temperature to reflux.

Next, if the dipeptide is bound to a solid support, it is removed from the solid support using standard procedures well known in the art. The conditions effective to remove the dipeptide from the solid support will be depend on the solid support and linker chosen. Generally, the peptide will be removed by acid hydrolysis using a strong acid, such as trifluoroacetic acid.

The dipeptide is then cyclized to form a diketopiperazine; this diketopiperazine will have the side-chain carboxyl of the aspartic acid or glutamic acid derivative still in the ester form. Cyclization is accomplished by heating the dipeptide under neutral conditions. Typically, the dipeptide will be heated at from about 80° C. to about 180° C., preferably at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). Preferably, the alcohol is butan-2-ol, and the azeotropic co-solvent is toluene. The heating is continued until the reaction is complete, and such times can be determined empirically. Typically, the dipeptide will be cyclized by refluxing it for about 8-24 hours, preferably about 18 hours.

Finally, the $R^5$ group is removed from the diketopiperazine by methods well known in the art for removing protecting groups (see above). When the $R^5$ group is benzyl, it is preferably removed from the diketopiperazine by hydrogenation using a palladium on carbon (Pd/C) catalyst. The use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided, in order to maintain the chirality of the final compound.

Once the $R^5$ group has been removed, the free acid can be derivatized, if desired, to form standard derivatives, such as amides and esters. Methods which can be used to convert the free acid to an amide or ester are well known in the art.

The physiologically-acceptable salts of the diketopiperzines of formula (1) may also be used in the practice of the invention. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

A diketopiperazine of formula (1), or a physiologically-acceptable salt thereof, can be used to treat a disease or condition mediated by PAF. To do so, a diketopiperazine of formula (1), or a physiologically-acceptable salt thereof, is administered to an animal in need of treatment. Preferably, the animal is a mammal, such as a rabbit, goat, dog, cat, horse or human. Effective dosage forms, modes of administration and dosage amounts for the various compounds of the invention may be determined empirically, and making such determinations is within the skill of the art. It is understood by those skilled in the art that the dosage amount will vary with the particular compound employed, the disease or condition to be treated, the severity of the disease or condition, the route(s) of administration, the rate of excretion of the compound, the duration of the treatment, the identify of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved.

The compounds of the present invention (i.e., diketopiperazines of formula (1) and physiologically-acceptable salts thereof) may be administered to an animal patient for therapy by any suitable route of administration, including orally, nasally, rectally, vaginally, parenterally (e.g., intravenously, intraspinally, intraperitoneally, subcutaneously, or intramuscularly), intracisternally, transdermally, intracranially, intracerebrally, and topically (including buccally and sublingually). The preferred routes of administration are orally and intravenously.

While it is possible for a compound of the present invention to be administered alone, it is preferable to administer the compound as a pharmaceutical formulation (composition). The pharmaceutical compositions of the invention comprise a compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

As noted above, PAF has been reported to play a role in a variety of diseases and conditions. These diseases and conditions include acute respiratory distress syndrome, allergies, arthritis, asthma, autoimmune diseases, bronchitis, cardiovascular disease, Crohn's disease, cystic fibrosis, emphysema, gastrointestinal ulceration, inflammation, inflammatory bowel disease, ischemia, multiple organ dysfunction syndrome, myocardial infarction, neoplastic diseases, ophthalmic inflammation, pain, psoriasis, respiratory infections, sepsis, shock, and ulcerative colitis. PAF also mediates platelet aggregation. The diketopiperzines of formula (1) can be used to treat any of these diseases and conditions and any other diseases and conditions in which PAF plays a role. The compounds of the invention can be given in combination with other standard therapies for a given disease or condition.

PAF has been reported to induce the production and secretion of interleukin 8 (IL-8) (see discussion in Example 3 below). IL-8 is a pro-inflammatory cytokine which has been reported to play a role in the pathogenesis of a large number of diseases and conditions, including acute respiratory distress syndrome, allergies, arthritis, asthma, autoimmune diseases, bronchitis, cancer, Crohn's disease, cystic fibrosis, emphysema, endocarditis, gastritis, inflammatory bowel disease, ischemia reperfusion, multiple organ dysfunction syndrome, nephritis, pancreatitis, respiratory viral infections, sepsis, shock, ulcerative colitis, and other inflammatory disorders. The diketopiperazines of formula (1) have been found to inhibit the PAF-induced production and/or release of IL-8. Preliminary data indicate that they also inhibit the production and/or release of IL-8 in the absence of PAF. In particular, it has been found that the lipopolysaccharide (LPS)-induced production and/or release of IL-8 by normal human bronchial epithelial cells is inhibited (data not shown). Thus, the diketopiperazines of the invention appear to act by two different mechanisms and may be used to treat diseases or conditions mediated by IL-8, as well as PAF.

EXAMPLES

Example 1

Preparation of
3-Methyl-2,5-Diketopiperazine-6-Acetic Acid (5)

Wang resin having 9-fluorenylmethyloxycarbonyl-protected alanine (Ala-Fmoc) attached thereto (3 grams (g), 2.52 mmol, 1 equivalent, NovaBiochem) was transferred to a clean round-bottom, 100 mL flask, and a solution of piperidine (12 mL) in dimethylformamide (DMF; 18 mL) was added to the resin in the flask. The solution was swirled for 1 hour, and the resin was isolated in a sintered glass funnel. The resin was washed with DMF (3×30 mL) followed by dichloromethane (DCM; 3×30 mL) and allowed to dry under vacuum for 5 minutes.

The partially-dried resin was transferred into a clean round-bottom, 100 mL flask, and DMF (10 mL) was added. Then, Boc-Asp(OBz)OH (3.25 g, 10.07 mmol, 4 equivalents) was added, followed by diisopropylamine (2.83 mL, 2.04 g, 20.19 mmol, 8 equivalents) and 2-(1H-benzotriazole-1-yl)-1,2,3,3-tetramethyluroniumtetrafluoroborate (TBTU; 3.24 g, 10.09 mmol, 4 equivalents, Acros). The slurry was allowed to react under anaerobic conditions over 12 hours. At the end of this time, the resin showed a negative ninhydrin test, indicating the completion of the coupling reaction. The resin was vacuum filtered and washed with DMF (3×30 mL) followed by DCM (3×30 mL). The resin was allowed to dry at room temperature under vacuum for 10 minutes before transferring it into a clean round-bottom, 100 mL flask.

Trifluoroacetic acid (TFA; 16.5 mL) was added to the dried resin and, upon its addition, the resin turned a red color. After swirling the resin for a further 30 minutes, TFA was removed by filtration, and the resin was washed with DCM (4×20 mL). The organic components were pooled, and toluene (20 mL) was added. The combined organic materials were evaporated to dryness under vacuum. Traces of TFA were removed by the addition of toluene and evaporation. The process was repeated until all TFA had been removed. This procedure resulted in a product as a pale yellow oil whose NMR and mass spectrophotometric data were consistent with the expected dipeptide benzyl ester whose structure (3) is shown below.

The dipeptide 3 was dissolved in butan-2-ol (40 mL) and diluted with toluene (60 mL). This solution was allowed to reflux for 24 hours. At the end of this period, the solution was allowed to cool to room temperature. It was then concentrated on a rotary evaporator, while maintaining the temperature at 50° C. Upon concentration, a white solid precipitated, and the precipitate was removed by filtration. The precipitate was washed with toluene (10 mL) and dried. The residue (0.650 g) gave a negative ninhydrin test. It was, then, crystallized from hot methanol. The spectroscopic and analytical results for the crystallized product confirmed its structure to be the desired compound—Asp-Ala diketopiperazine-benzyl ester shown below (4).

This compound (400 mg) was dissolved in methanol (250 mL), and palladium on carbon catalyst (Pd/C; 10%, 0.4 g) was added carefully. The flask was purged with hydrogen and kept at a positive hydrogen pressure. The solution was kept in this atmosphere for at least 4 hours. The catalyst was removed with a filtering aid (celite) and washed with methanol. The methanol washings were combined, and the solvent was removed (yield 200 mg). Mass spectrometer and NMR analysis showed that the free acid Asp-Ala diketopiperazine (3-methyl-2,5-diketopiperazine-6-acetic acid, 5) had formed without any cross contamination.

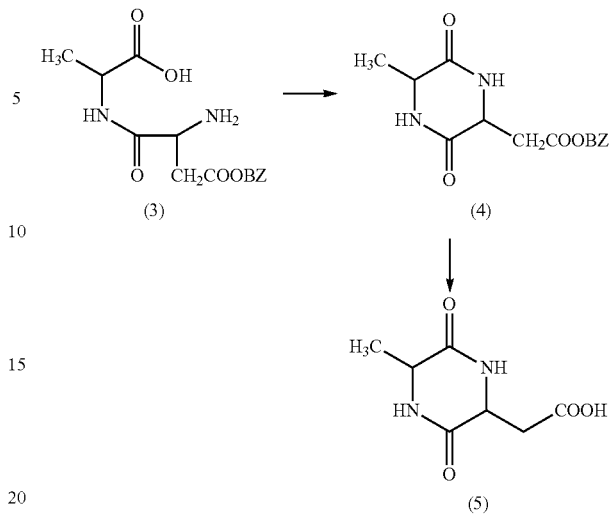

Example 2

Preparation of Asp-Ala Diketopiperazine Amide (6)

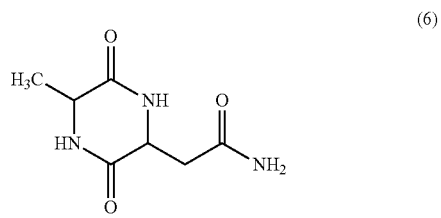

To a solution of 3-methyl-2,5-diketopiperazine-6-acetic acid (0.151 g, 0.81 mmol, 1 equivalent, preparation described in Example 1, 5) in DMF (2.5 mL) was added carbonyl diimidazole (0.26 g, 1.60 mmol, 2 equivalents, Aldrich). After stirring at room temperature for 1 hour, solid ammonium acetate (0.63 g, 8.17 mmol, 10 equivalents, Aldrich) was added. Stirring at room temperature was continued overnight, at which time the reaction was partitioned between water (20 mL) and ethyl acetate (10 mL). The aqueous layer was washed with a second aliquot of ethyl acetate (10 mL) and then evaporated to dryness under reduced pressure (61° C.). Traces of DMF were removed by further co-evaporations with water and then toluene to give a white solid (362 mg). This was taken up into a minimum volume of methanol in DCM (20:80 v/v). The solvent eluted was fractionated, and the appropriate fractions were pooled and evaporated under reduced pressure (40° C.) to give a white solid. The product was then recrystallized from methanol to given the desired product (0.116 g, 76% yield, 6).

Example 3

Inhibition of Release of IL-8

Interleukin 8 (IL-8) is a pro-inflammatory cytokine and a potent chemoattractant and activator of neutrophils. It has also been reported to be a chemoattractant and activator of T-lymphocytes and eosinophils. IL-8 is produced by immune cells (including lymphocytes, neutrophils, monocytes and macrophages), fibroblasts and epithelial cells. Reports indicate an important role for IL-8 in the pathogenesis of respiratory viral infections, asthma, bronchitis, emphysema, cystic fibrosis, acute respiratory distress syndrome, sepsis, multiple organ dysfunction syndrome, and other inflammatory disorders.

It has been reported that PAF induces the transcription and secretion of IL-8 in human lung fibroblasts. Roth et al., *J. Exp. Med.*, 184, 191-201 (1996). It has also been reported that PAF enhances the production of IL-8 by human mononuclear cells in response to lipopolysaccharide (LPS), but that PAF alone only weakly induces the production of IL-8 by these cells. Arbabi et al., *Archives Surgery*, 134, 1348-1353 (1999). These authors hypothesize that PAF "primes" the innate immune system to produce enhanced amounts of proinflammatory mediators in response to a second inflammatory stimulus that otherwise would have been insufficient to trigger an inflammatory response. They further speculate that if this priming is generalized, it may become harmful. In such a case, the second stimulus, which would be considered minor by the unprimed innate immune system, would induce an aggressive, diffuse, and nonfocused release of inflammatory mediators, possibly leading to multiple organ dysfunction syndrome.

NHBE 6122 normal human bronchial epithelial cells (Clonetics, San Diego, Calif.) were added to a 24-well tissue culture plate (Falcon, now BD Biosciences, Franklin Lakes, N.J.) at 20,000 cells/well and allowed to adhere overnight (16-18 hours) in BEGM (bronchial epithelial growth medium; Clonetics) containing epinephrine (complete medium) at 37° C. and 5% $CO_2$. After adhering, the cells were washed twice with BEGM medium without epinephrine. They were then incubated in complete medium or in complete medium containing 20 μM 3-methyl-2,5-diketopiperazine-6-acetic acid (DA-DKP; preparation described in Example 1, 5; stock solution made in HEPES buffered saline (HBSS; Clonetics) at 4 mM for 20 minutes at 37° C. and 5% $CO_2$. Platelet activating factor (PAF; Sigma, St. Louis, Mo.) dissolved in dimethylsulfoxide (DMSO; tissue culture grade; Sigma, St. Louis, Mo.) was then added to a final concentration of 100 nM or 500 nM, and the cells were incubated for an additional 6 hours at 37° C. and 5% $CO_2$. Medium containing DMSO and HBSS was used as a control.

The concentration of IL-8 in cell supernatants was determined by an ELISA using human IL-8 matched pair antibodies (Endogen, Cambridge, Mass.). The ELISA was performed using an ELISA kit from Endogen, Cambridge, Mass. according to the manufacturer's instructions with the following exceptions: (1) coating antibody at 1 μg/ml; (2) detecting antibody 30 ng/ml; StrepAvidin HRP diluted 1:32,000.

The results are presented in Tables 1-3 below. As can be seen, IL-8 secretion induced by PAF in NHBE 6122 cells was inhibited by the pre-incubation of the cells with DA-DKP. It is hypothesized that the DA-DKP binds to PAF, the PAF receptor, or both, blocking the signal to produce (release) IL-8.

TABLE 1

|  | IL-8 (pg/ml) | SEM |
| --- | --- | --- |
| DMSO | 729.88 | 8.46 |
| HBSS | 809.62 | 198.23 |
| DA-DKP (20 μM) | 803.11 | 67.18 |
| PAF (100 nM) | 1094.68 | 103.21 |
| PAF + DA-DKP | 714.91 | 88.95 |

TABLE 2

|  | IL-8 (pg/ml) | SEM |
| --- | --- | --- |
| DMSO | 602.99 | 73.48 |
| HBSS | 581.86 | 64.36 |
| DA-DKP (20 μM) | 837.84 | 100.73 |
| PAF (500 nM) | 887.87 | 112.56 |
| PAF + DA-DKP | 542.5 | 37.17 |

TABLE 3*

|  | IL-8 (pg/ml) | SEM |
| --- | --- | --- |
| DMSO | 209.79 | 13.24 |
| HBSS | 233.08 | 5.79 |
| DA-DKP (20 μM) | 184.86 | 34.73 |
| PAF (100 nM) | 355.36 | 11.28 |
| PAF + DA-DKP | 201.93 | 20.64 |

*For Table 3, cells were split to give 5,000 cells/well four days prior to the experiment and were allowed to grow to 70% confluence.

We claim:

1. A pharmaceutical composition for inhibiting inflammation comprising a pharmaceutically-acceptable carrier and an amount of active ingredient effective to inhibit inflammation, wherein the active ingredient is 3-methyl-2,5-diketopiperazine-6-acetic acid or a physiologically-acceptable salt thereof, and wherein the composition is an isotonic formulation.

2. The pharmaceutical composition of claim 1, wherein the composition is formulated for parenteral administration.

3. The pharmaceutical composition of claim 1, wherein the composition is formulated for injection.

4. The pharmaceutical composition of claim 1, wherein the active ingredient is present in the composition at a concentration of at least about 20 μM.

5. The pharmaceutical composition of claim 1, wherein the active ingredient is present in the composition at a concentration of about 20 μM.

* * * * *